United States Patent [19]

McGahren et al.

[11] Patent Number: 5,606,040
[45] Date of Patent: Feb. 25, 1997

[54] ANTITUMOR AND ANTIBACTERIAL SUBSTITUTED DISULFIDE DERIVATIVES PREPARED FROM COMPOUNDS POSSESSING A METHYL-TRITHIO GROUP

[75] Inventors: William J. McGahren, Demarest, N.J.; Martin L. Sassiver, Spring Valley; George A. Ellestad, Pearl River, both of N.Y.

[73] Assignee: American Cyanamid Company, Wayne, N.J.

[21] Appl. No.: 155,179

[22] Filed: Nov. 15, 1993

Related U.S. Application Data

[63] Continuation of Ser. No. 825,248, Jan. 24, 1992, abandoned, which is a continuation of Ser. No. 339,323, Apr. 14, 1989, abandoned, which is a continuation-in-part of Ser. No. 246,247, Sep. 21, 1988, abandoned, which is a continuation-in-part of Ser. No. 114,940, Oct. 30, 1987, abandoned.

[51] Int. Cl.⁶ .................................................. C07H 15/00
[52] U.S. Cl. ...................... 536/17.6; 536/16.8; 536/17.5; 536/18.1
[58] Field of Search ...................... 536/16.8, 17.5, 536/17.6, 18.1, 18.6

*Primary Examiner*—Elli Peselev
*Attorney, Agent, or Firm*—H. G. Jackson; Elizabeth M. Barnhard

[57] ABSTRACT

This disclosure describes disulfide analogs of the family of antibacterial and antitumor agents known collectively as the LL-E33288 complex.

33 Claims, 23 Drawing Sheets

ANTITUMOR AND ANTIBACTERIAL SUBSTITUTED DISULFIDE DERIVATIVES PREPARED FROM COMPOUNDS POSSESSING A METHYL-TRITHIO GROUP

This is a continuation of application Ser. No. 07/825,248 filed on Jan. 24, 1992, now abandoned, which is a continuation of Ser. No. 07/339,323 filed on Apr. 14, 1989 (now abandoned) which is a continuation-in-part of application Ser. No. 246,247 filed Sep. 21, 1988 (now abandoned) which is a continuation-in-part of Ser. No. 114,940 filed Oct. 30, 1987 (now abandoned).

SUMMARY OF THE INVENTION

The invention is disulfide compounds of the $\alpha_1$, $\alpha_2$, $\alpha_3$, $\alpha_4$, $\beta_1$, $\beta_2$, $\gamma$, $\delta$ and pseudoaglycone components of the LL-33288 complex and derivatives thereof as well as the disulfide compounds of BBM-1675, FR-900405, FR-900406, PD114759, PD115028, CL-1577A, CL-1577B, CL-1577D, CL-1577E, CL-1724 antibiotics and derivatives thereof prepared by reacting the antibiotic with an unsubstituted or substituted alkyl mercaptan. These disulfide compounds are effective antitumor agents.

DESCRIPTION OF THE DRAWINGS

FIG. I is the ultraviolet spectrum of LL-E33288$\gamma_1'$.

FIG. II is the proton magnetic resonance spectrum of LL-E33288$\gamma_1'$.

Figure 1:
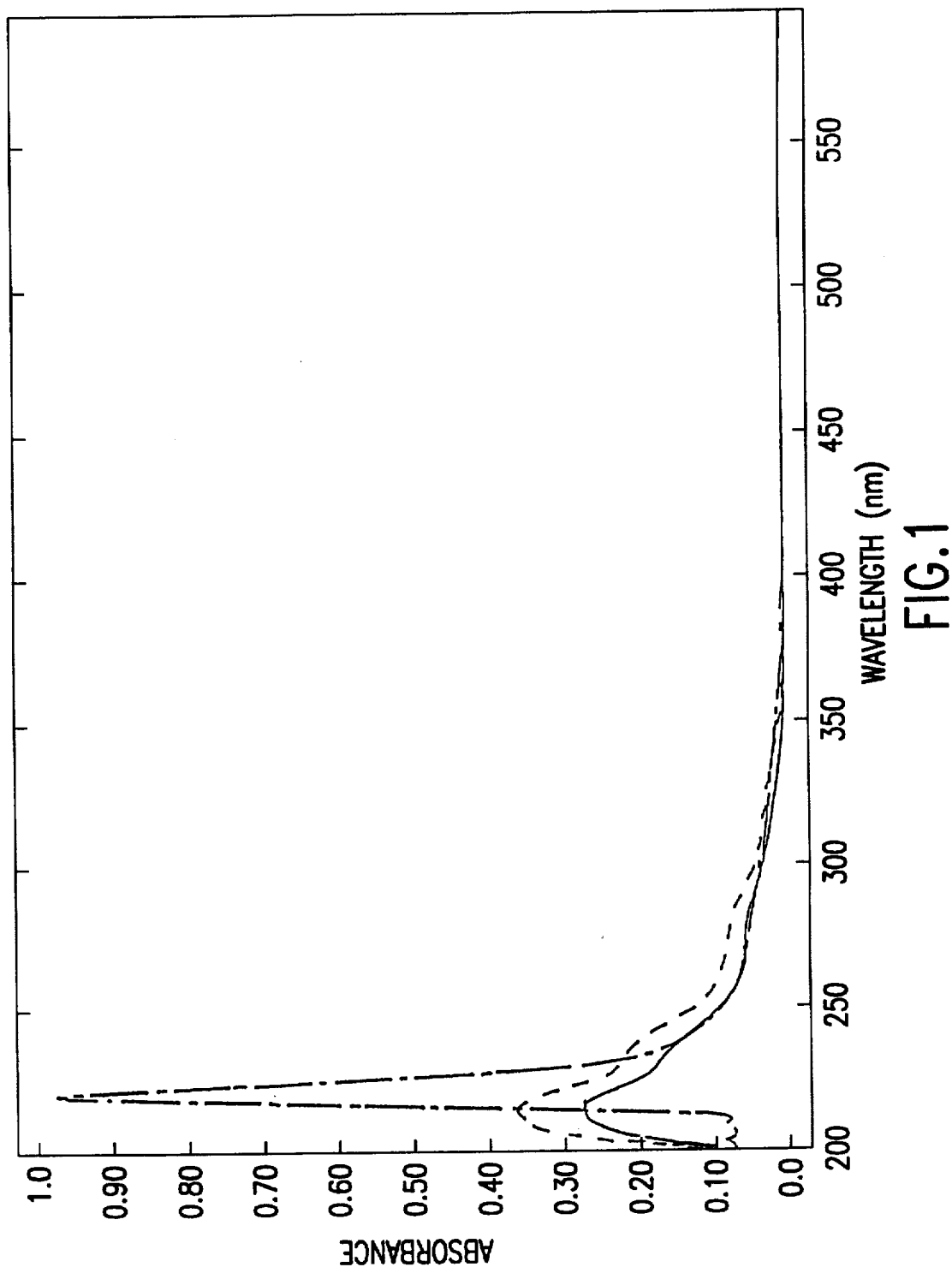
Figure 2:
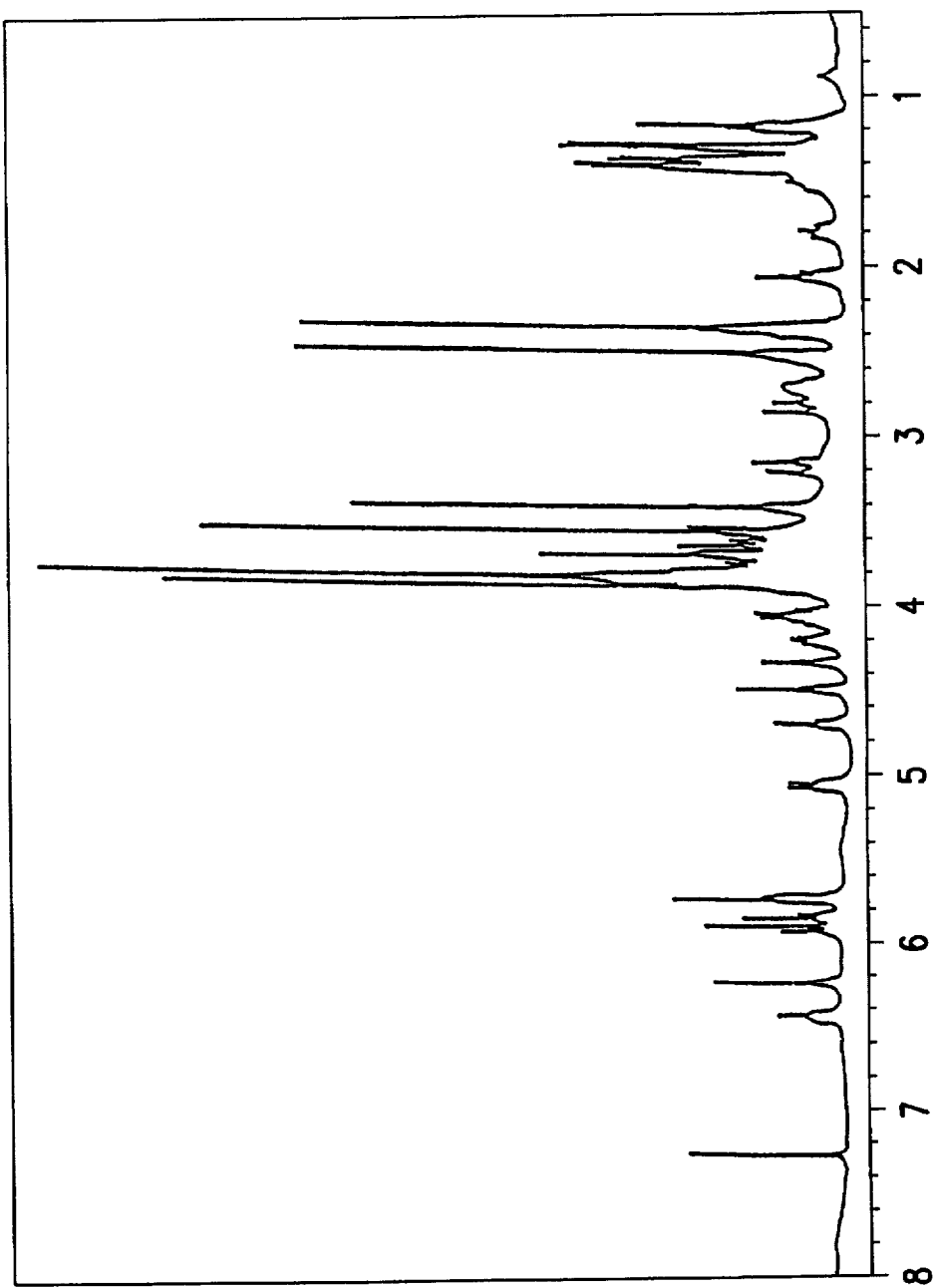
Figure 3:
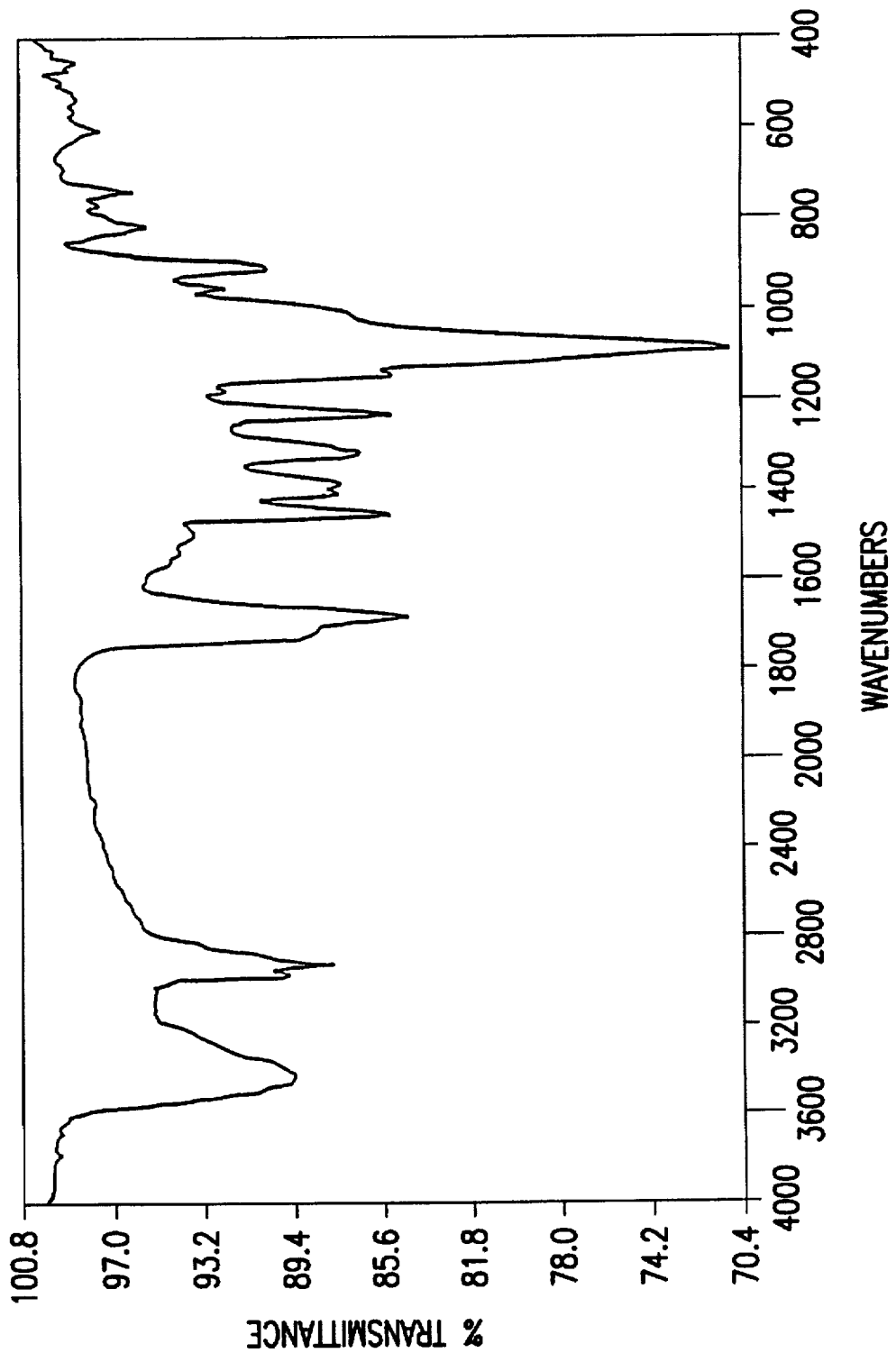
Figure 4:
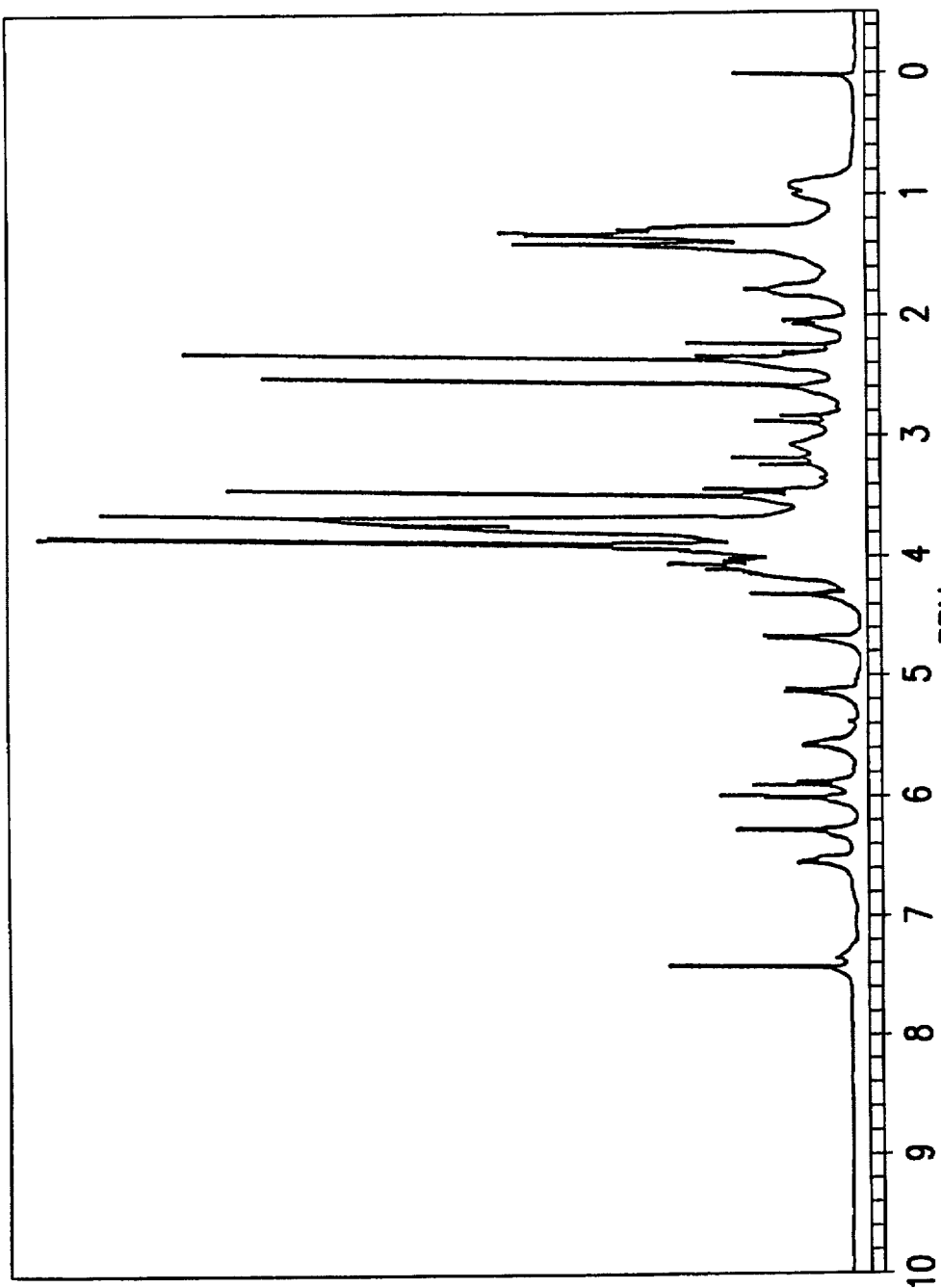
Figure 5:
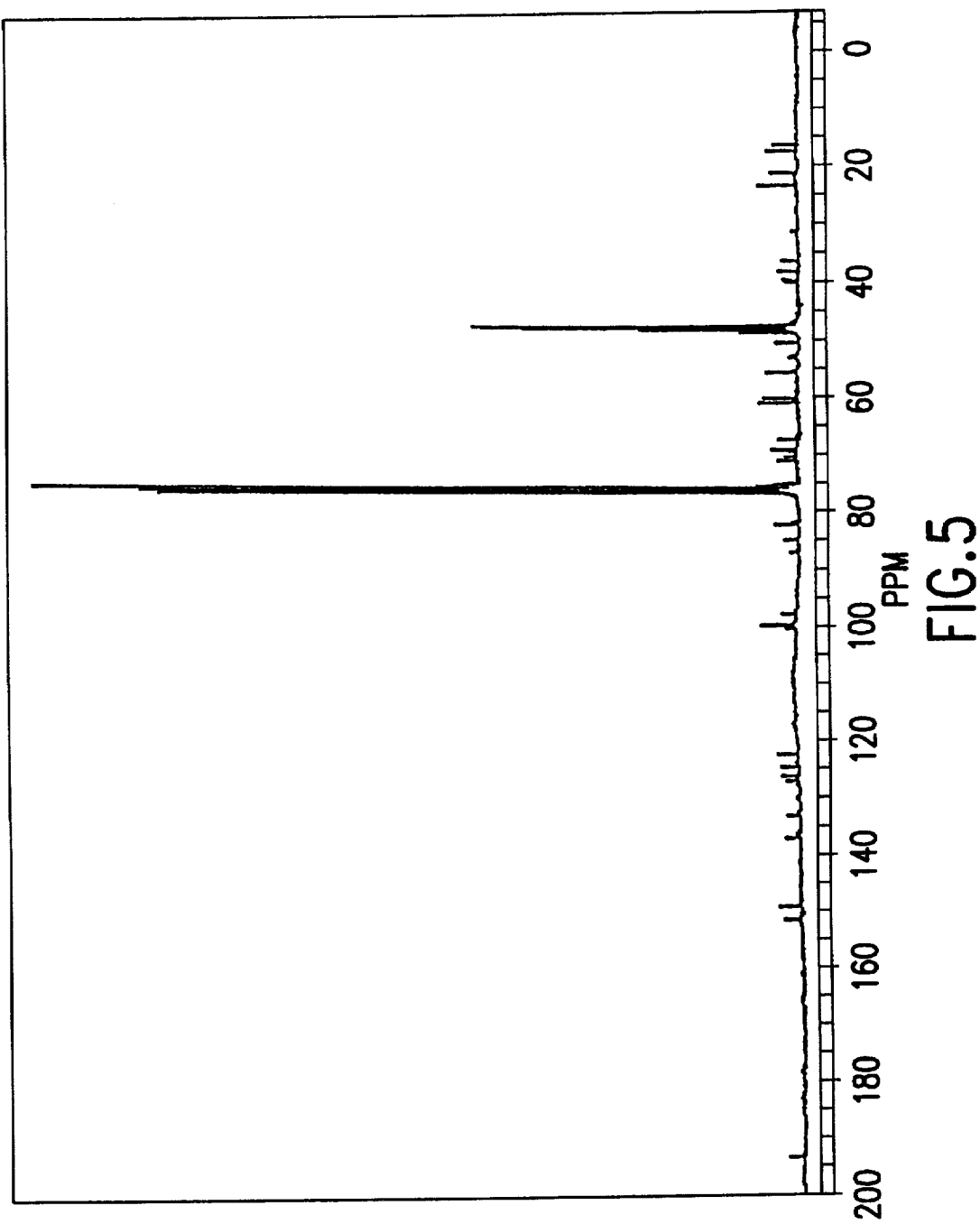
Figure 6:
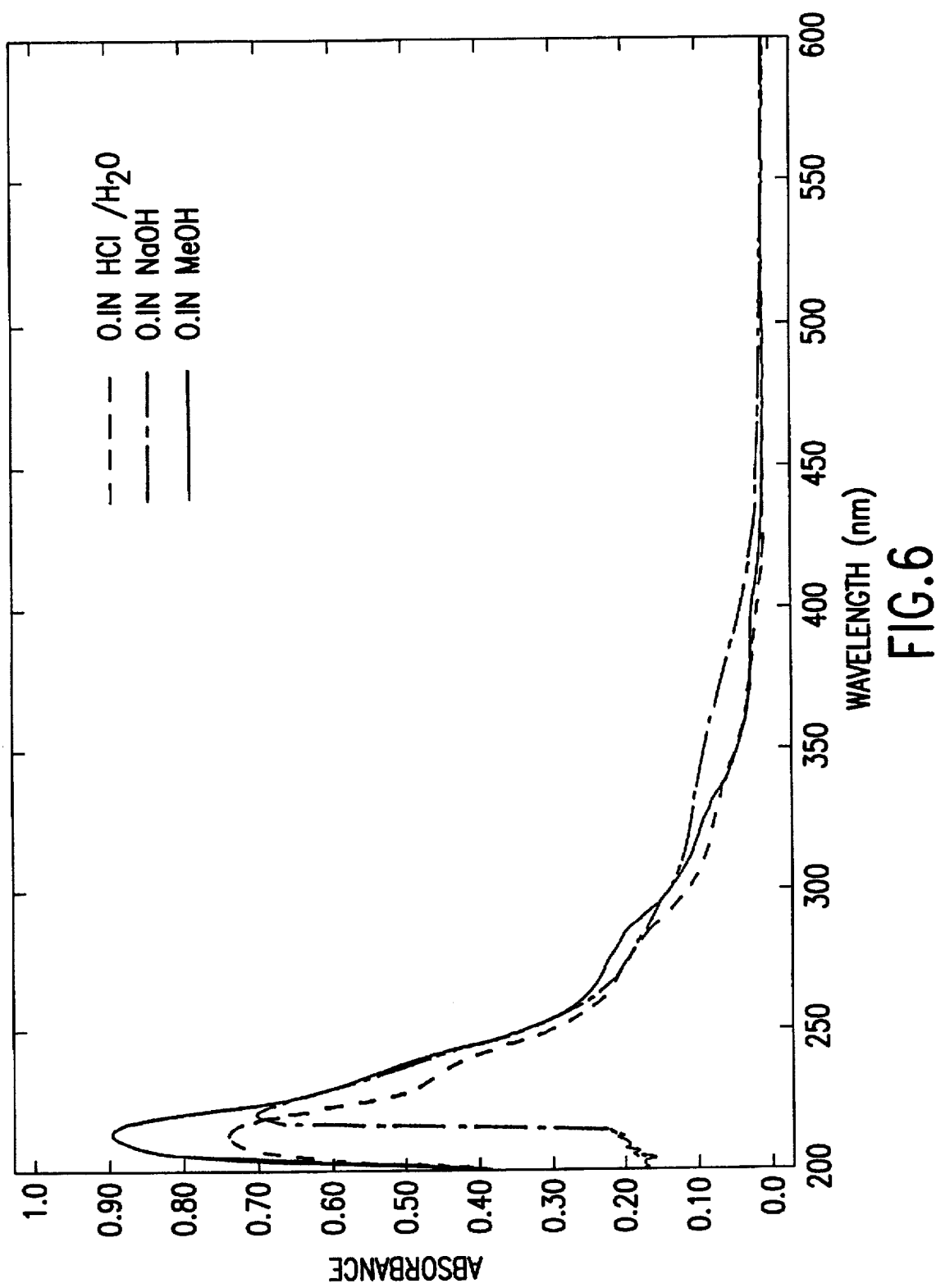
Figure 7:
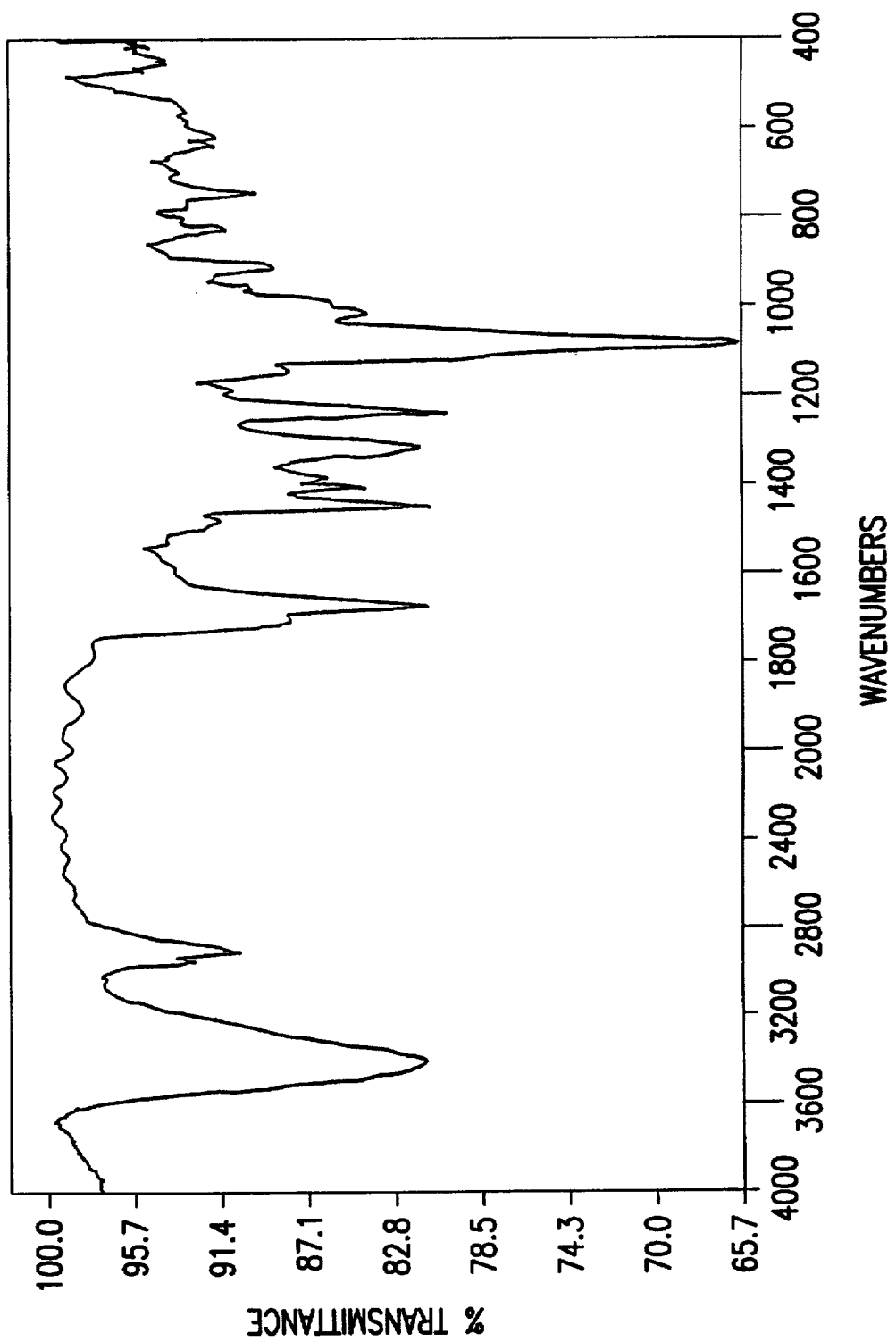
Figure 8:
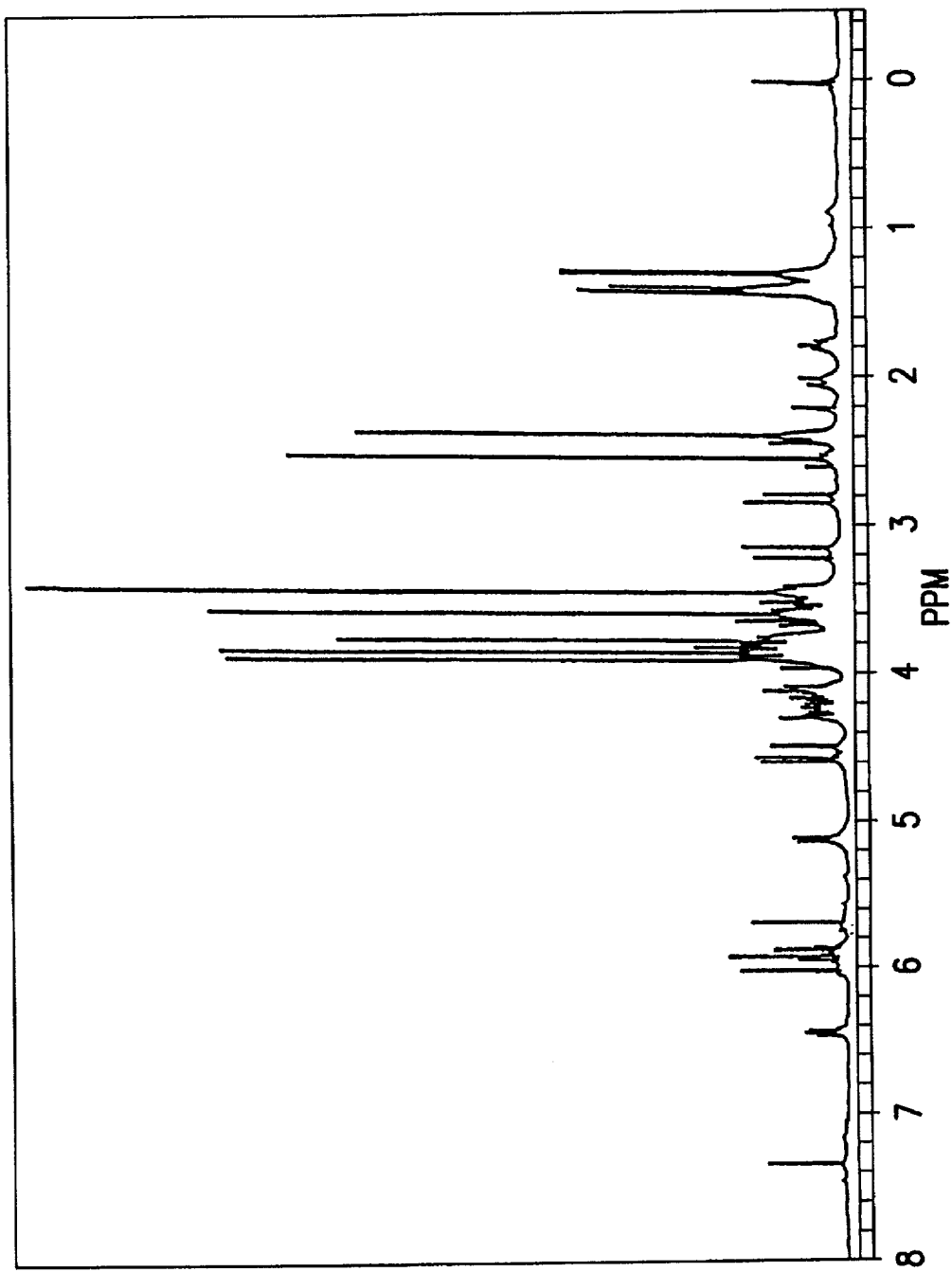
Figure 9:
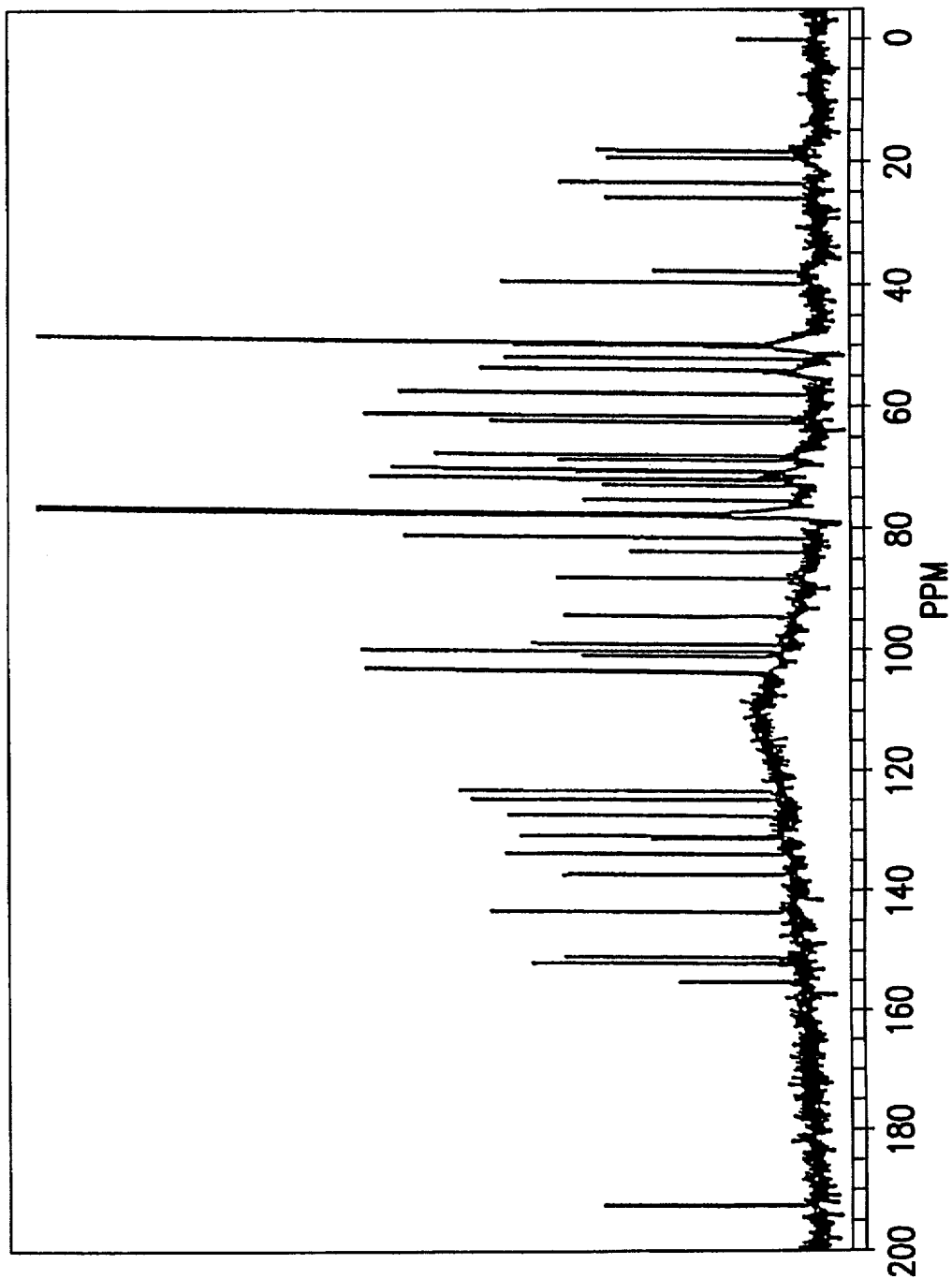
Figure 10:
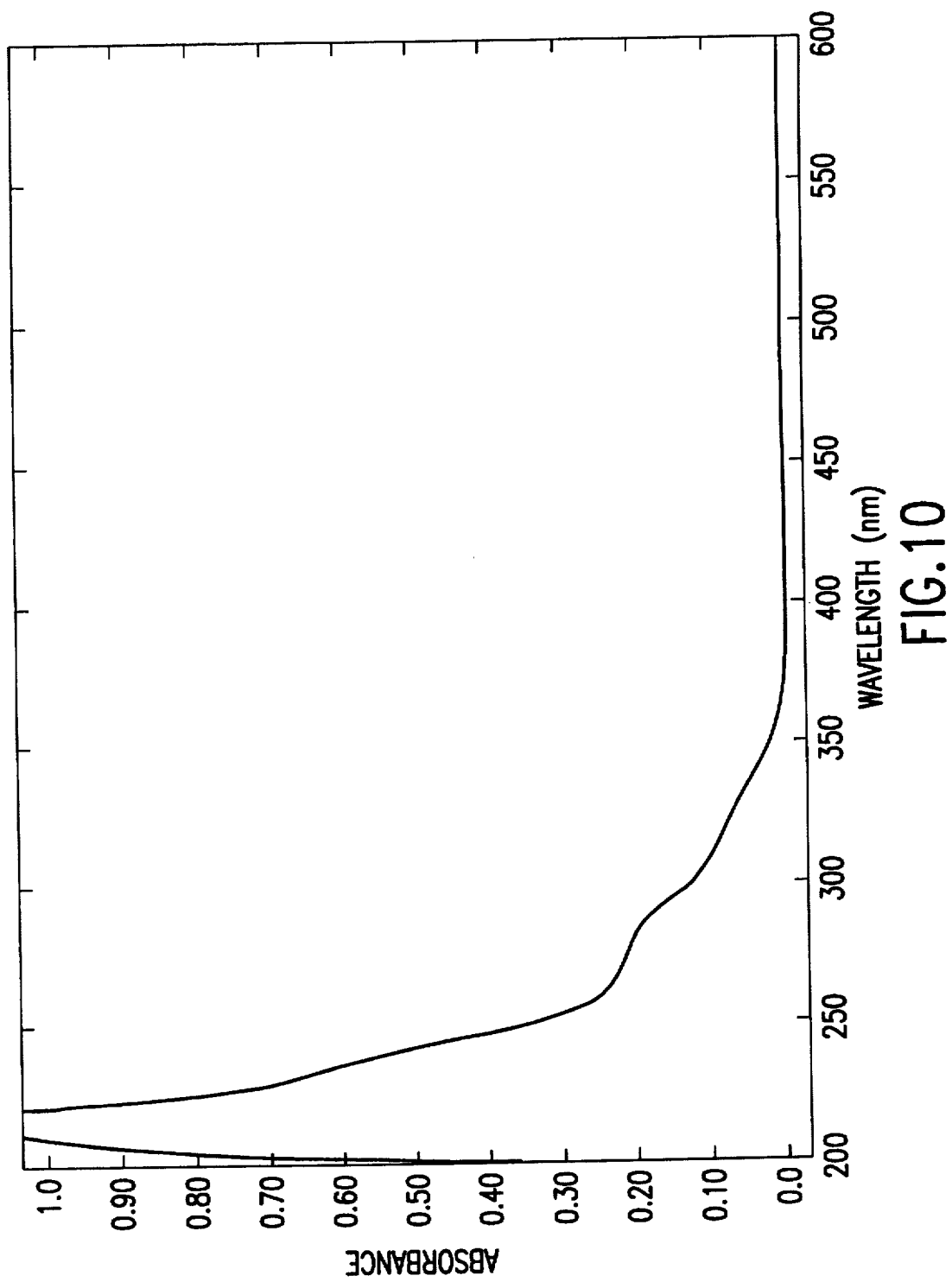
Figure 11:
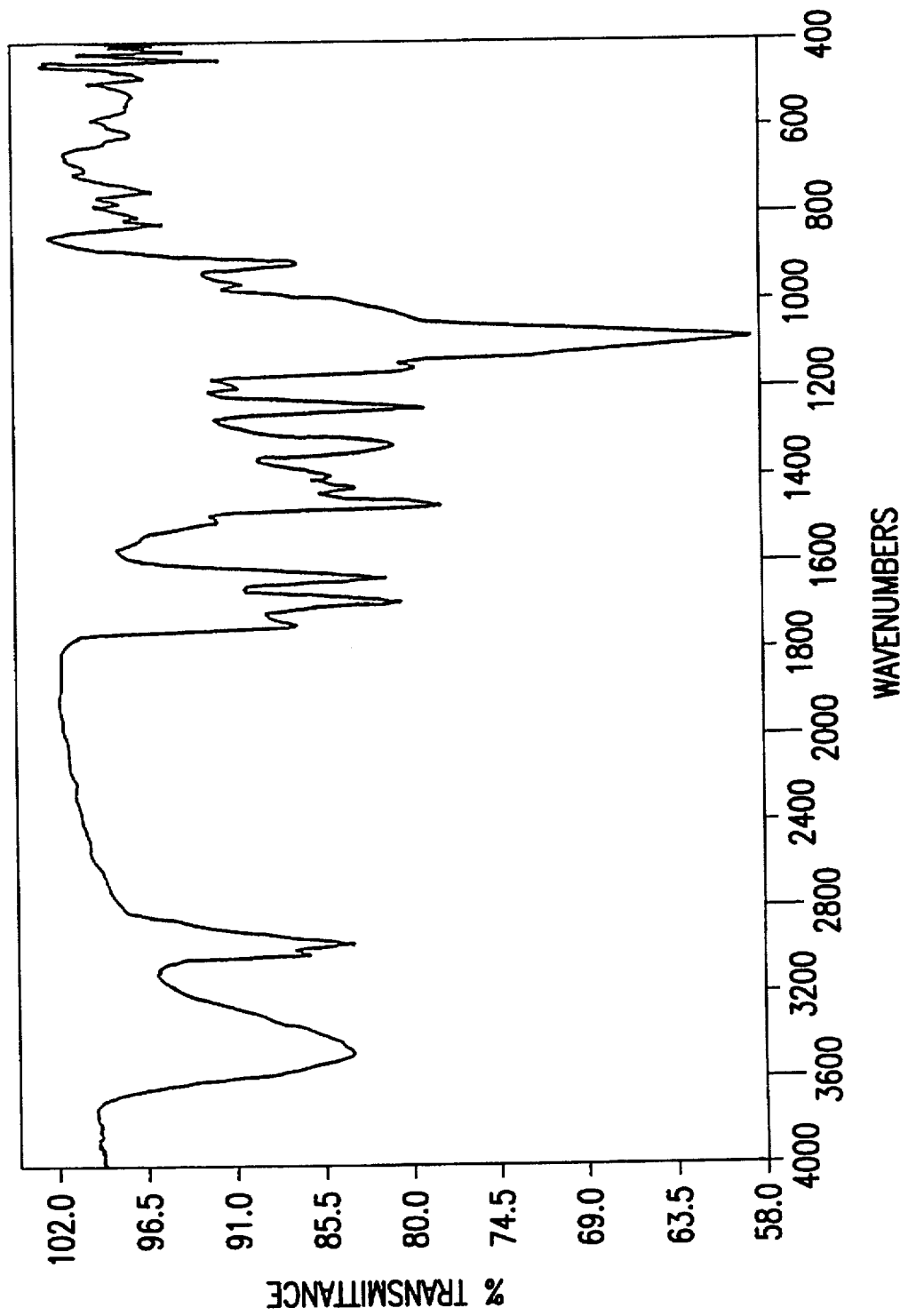
Figure 12:
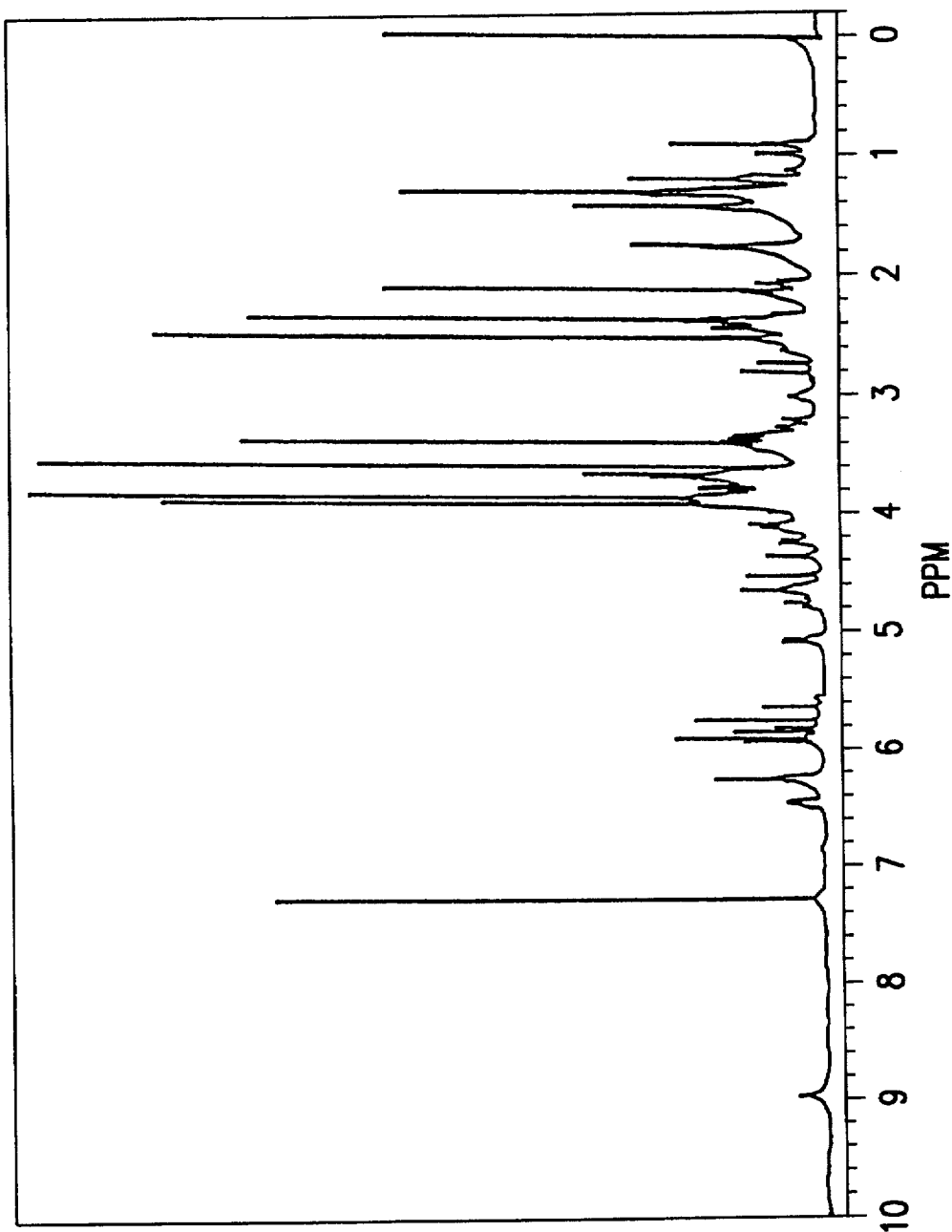
Figure 13:
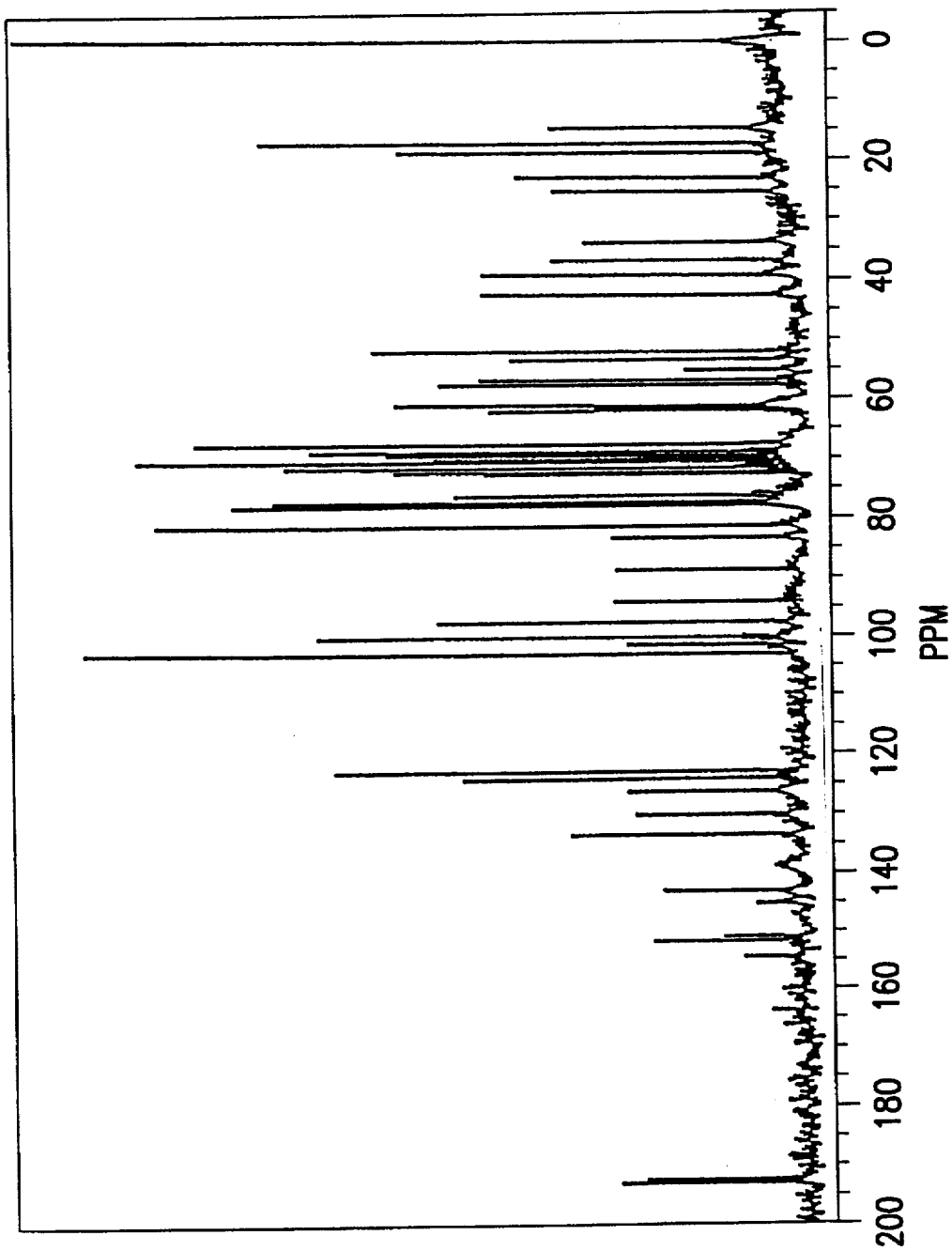
Figure 14:
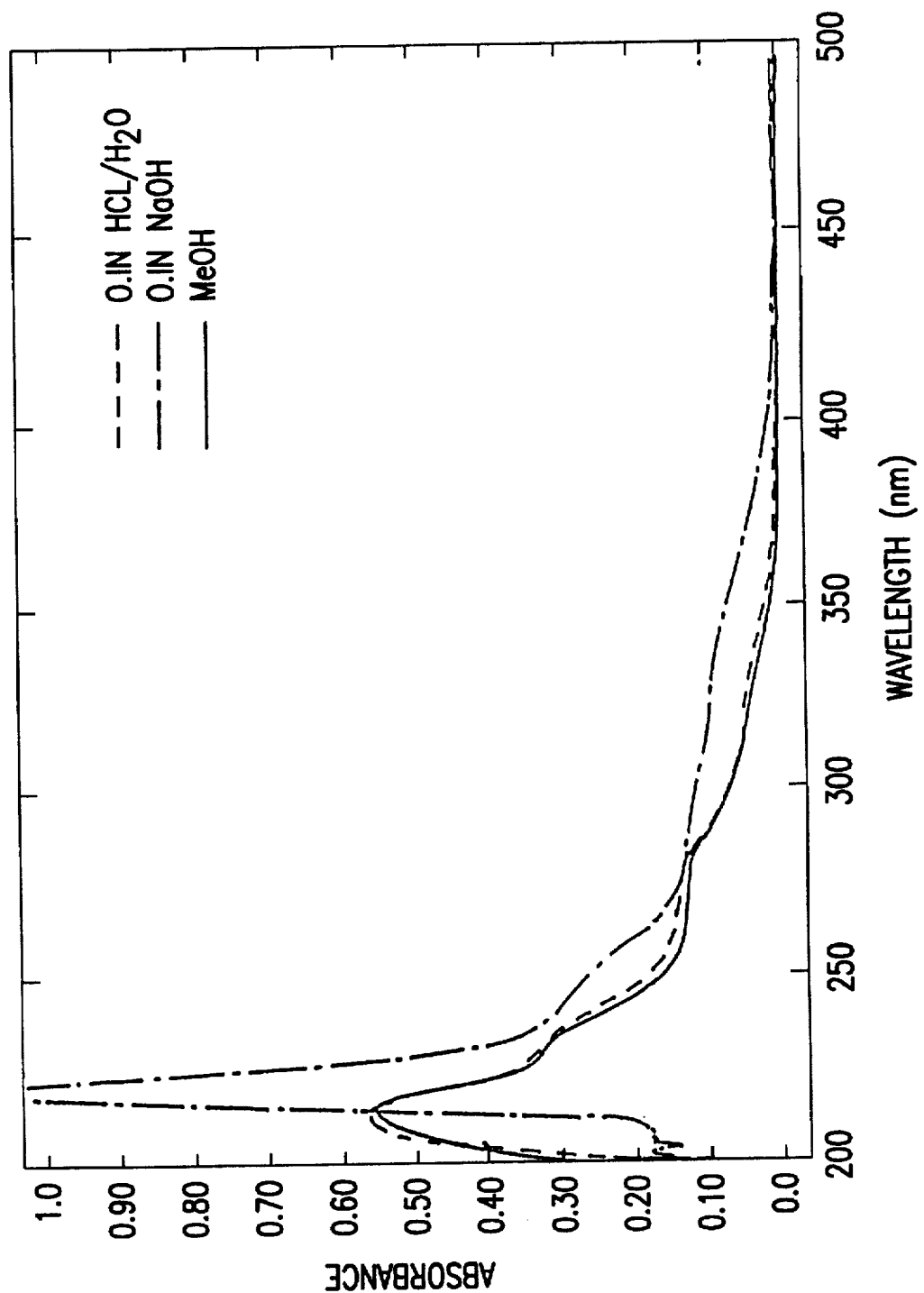
Figure 15:
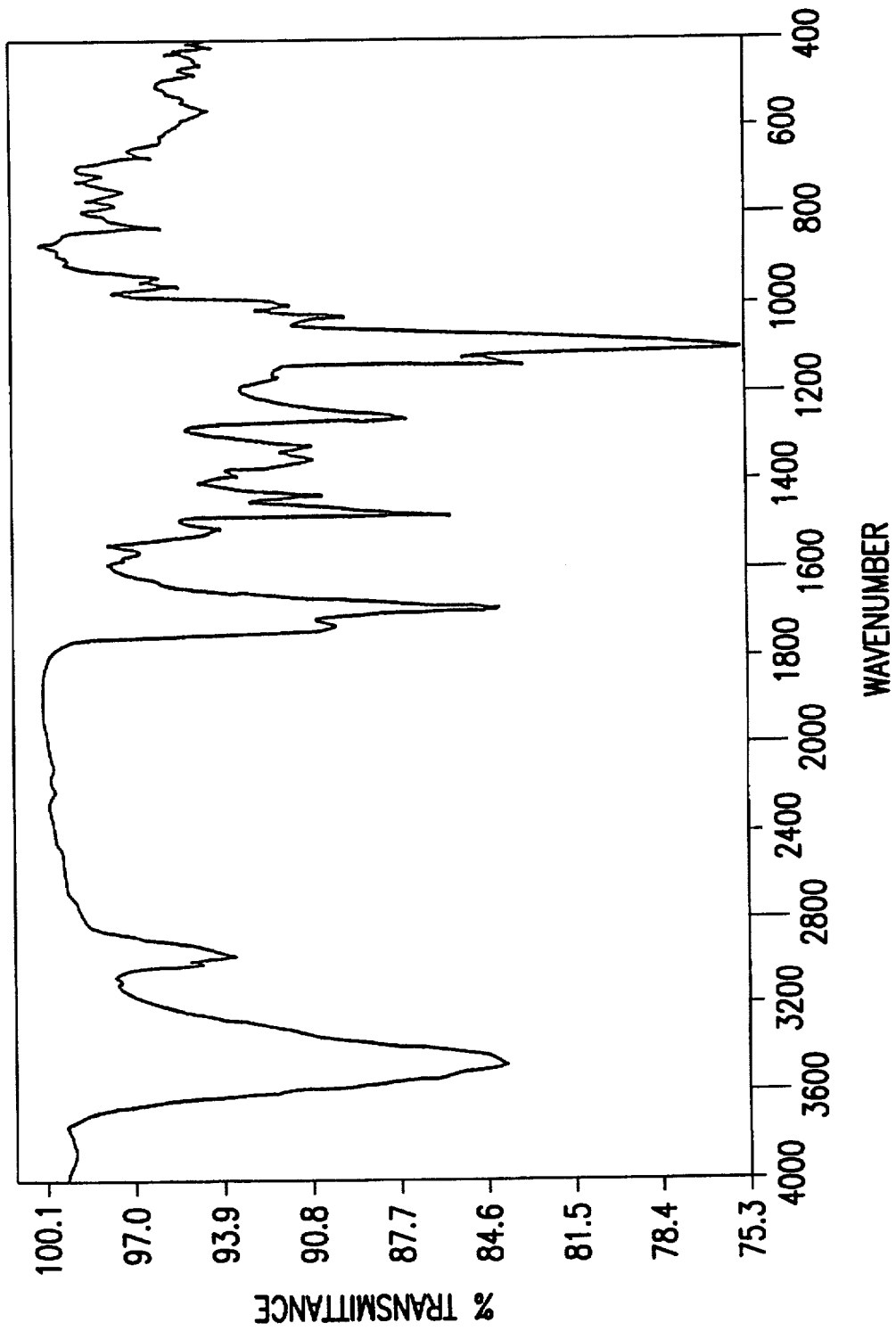
Figure 16:
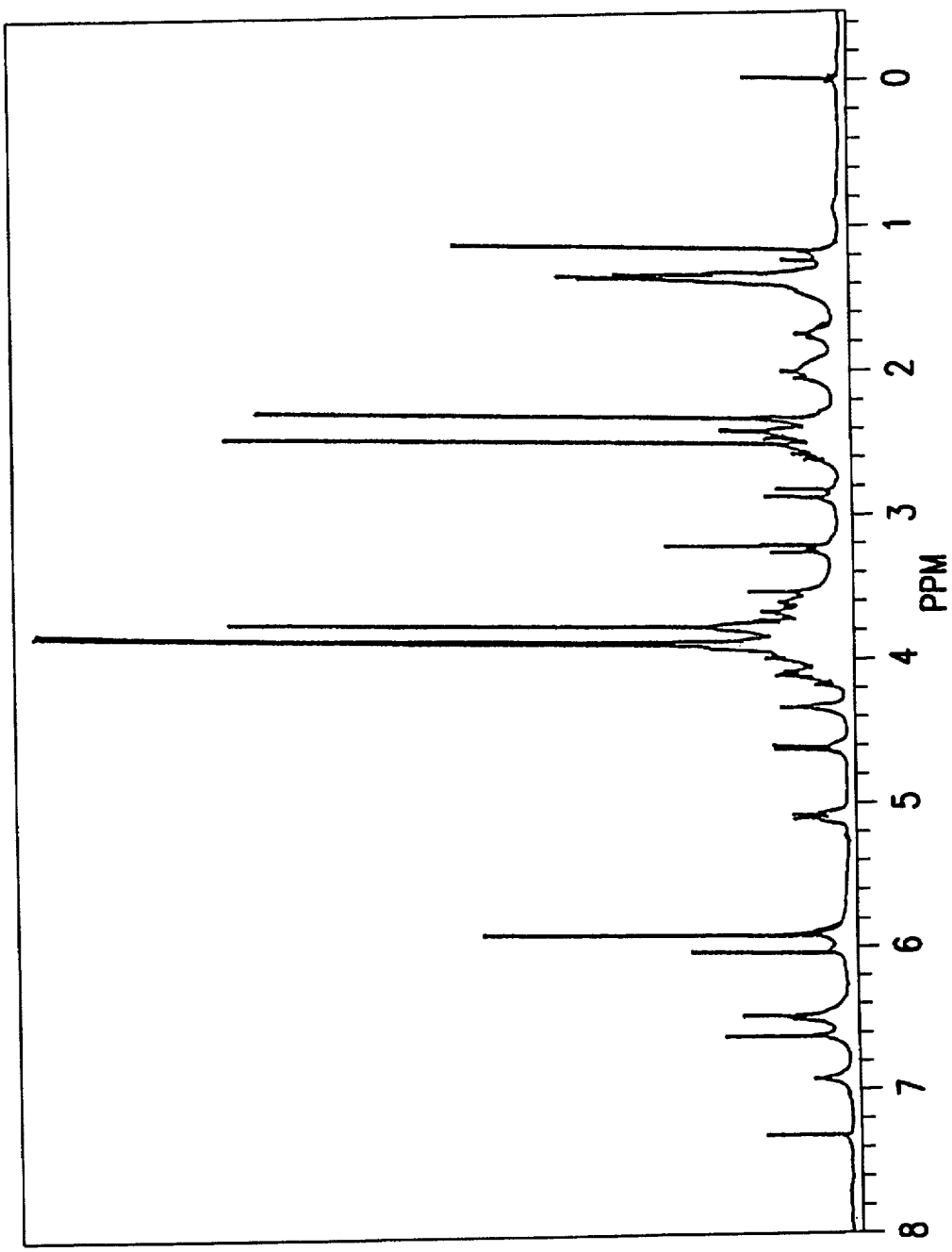
Figure 17:
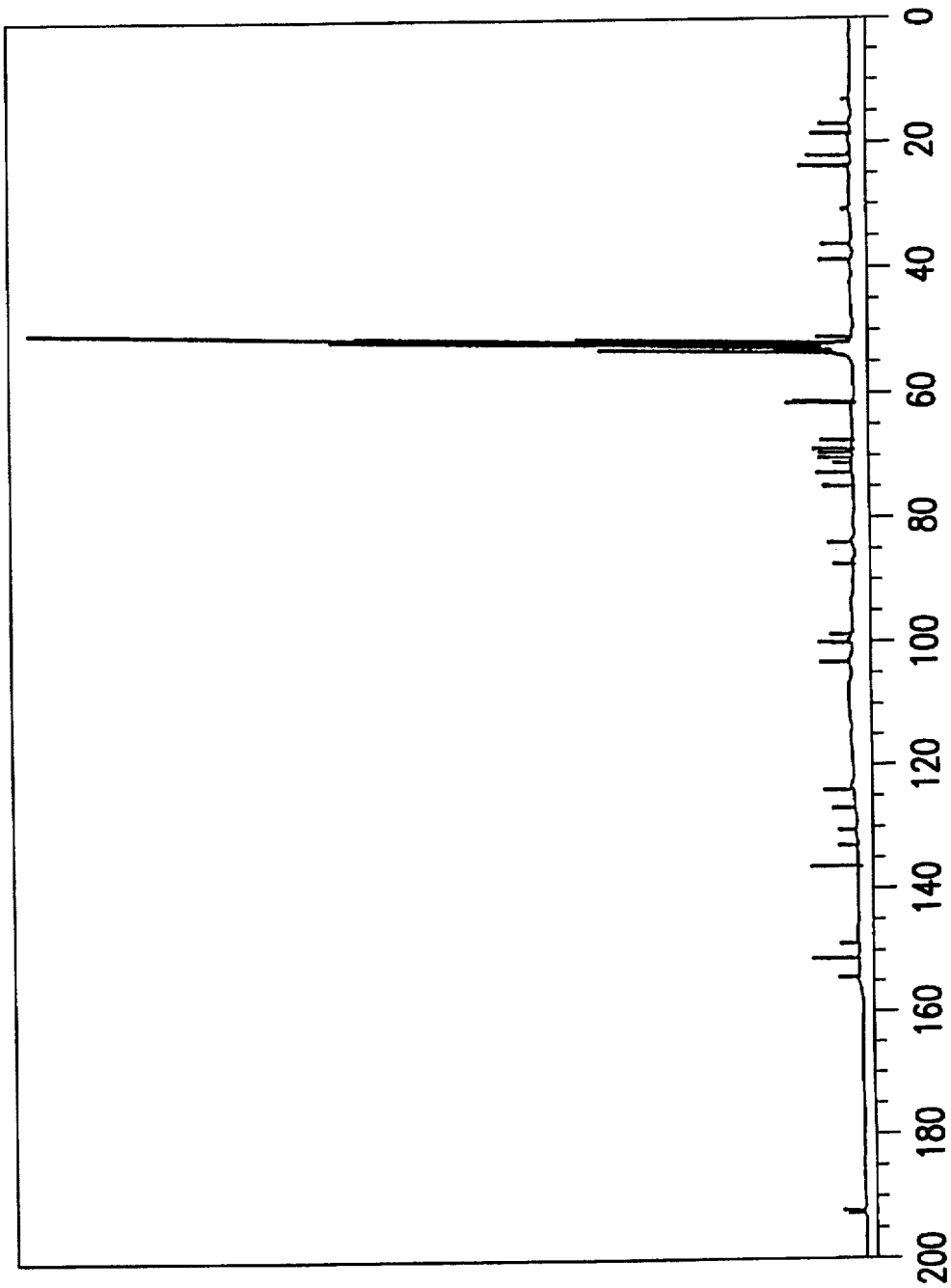
Figure 18:
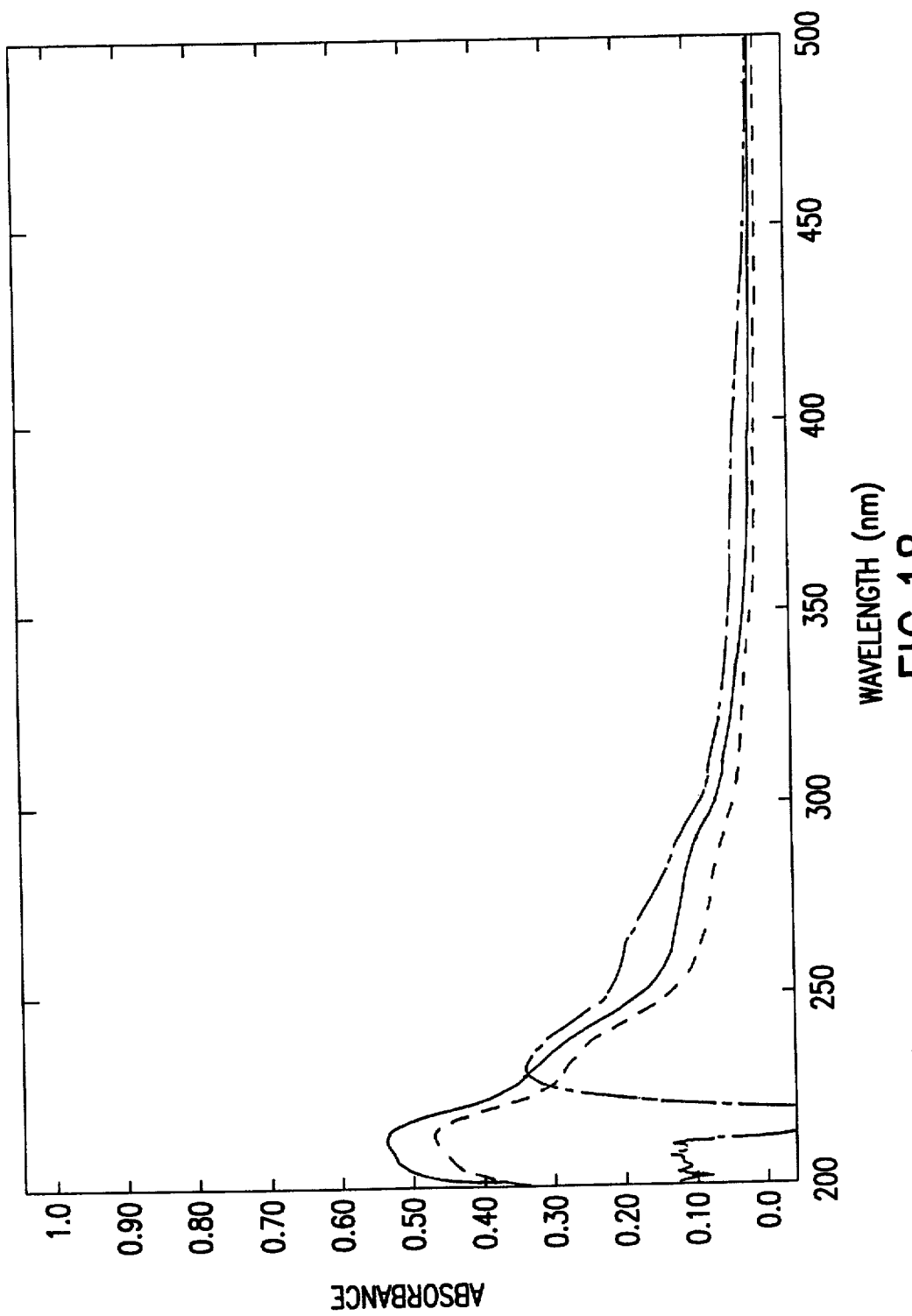
Figure 19:
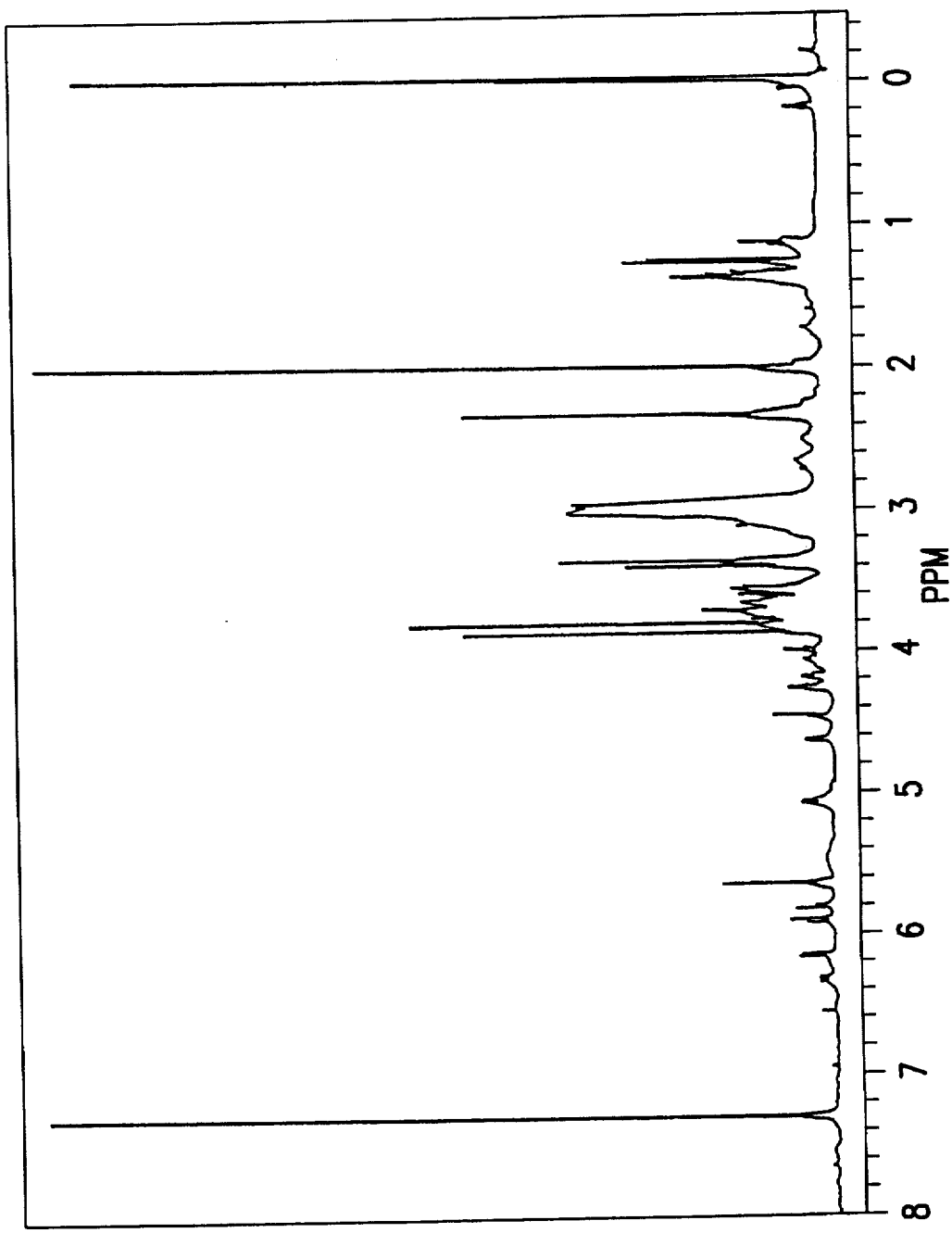
Figure 20:
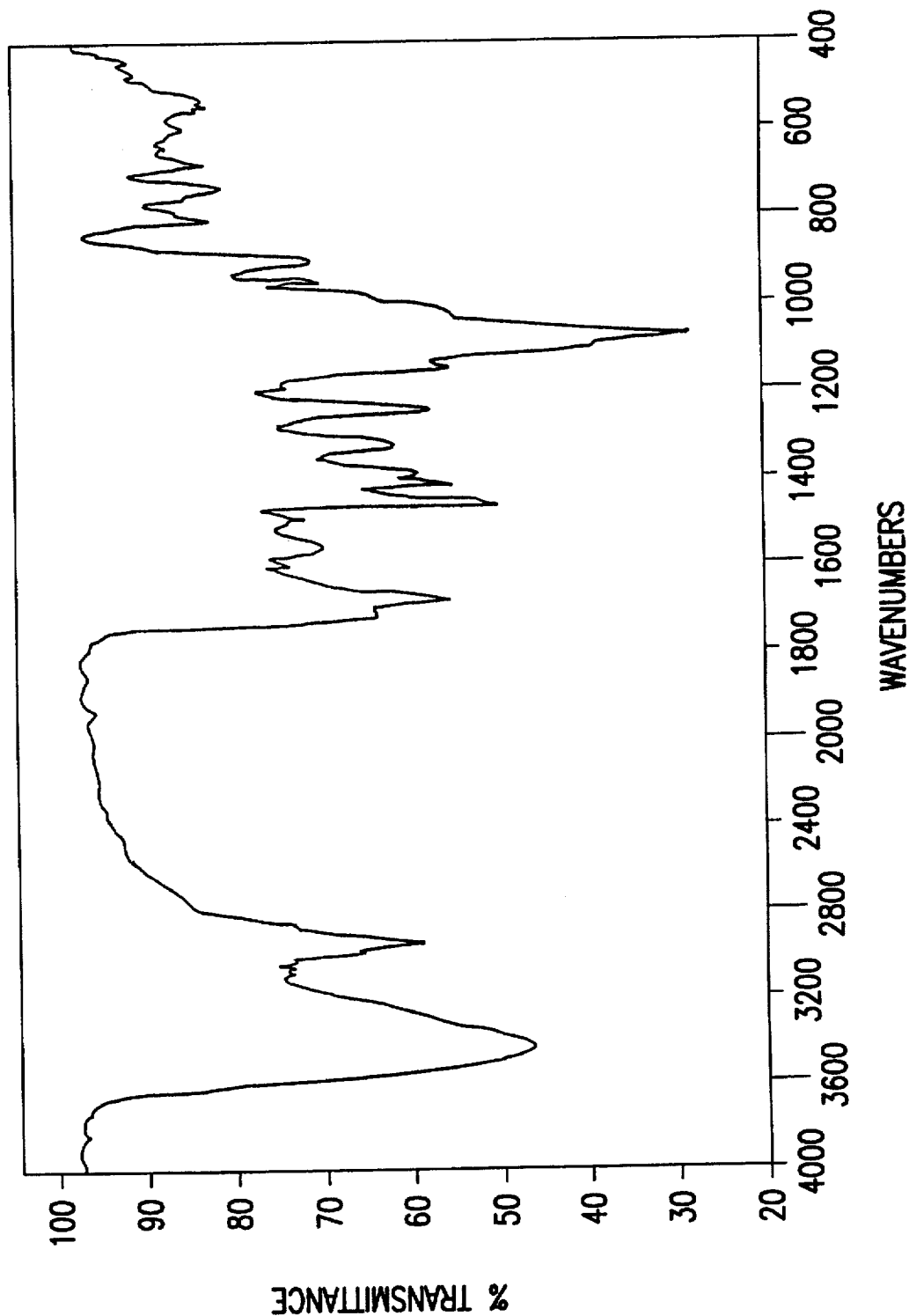
Figure 21A:
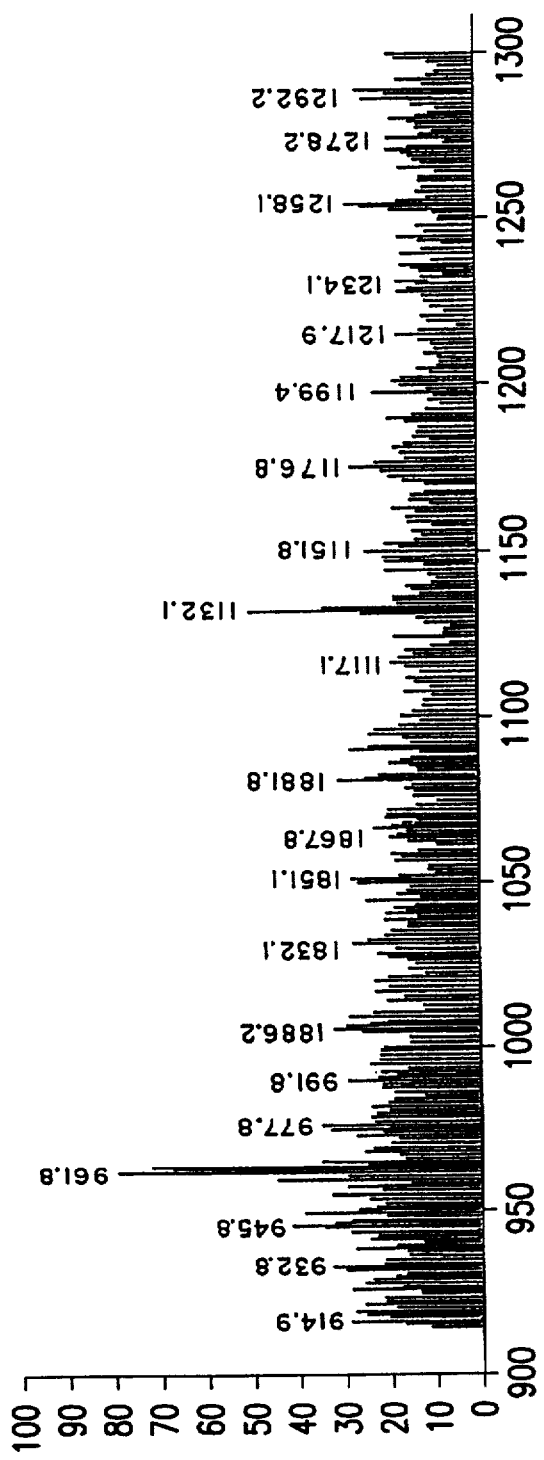
Figure 21B:
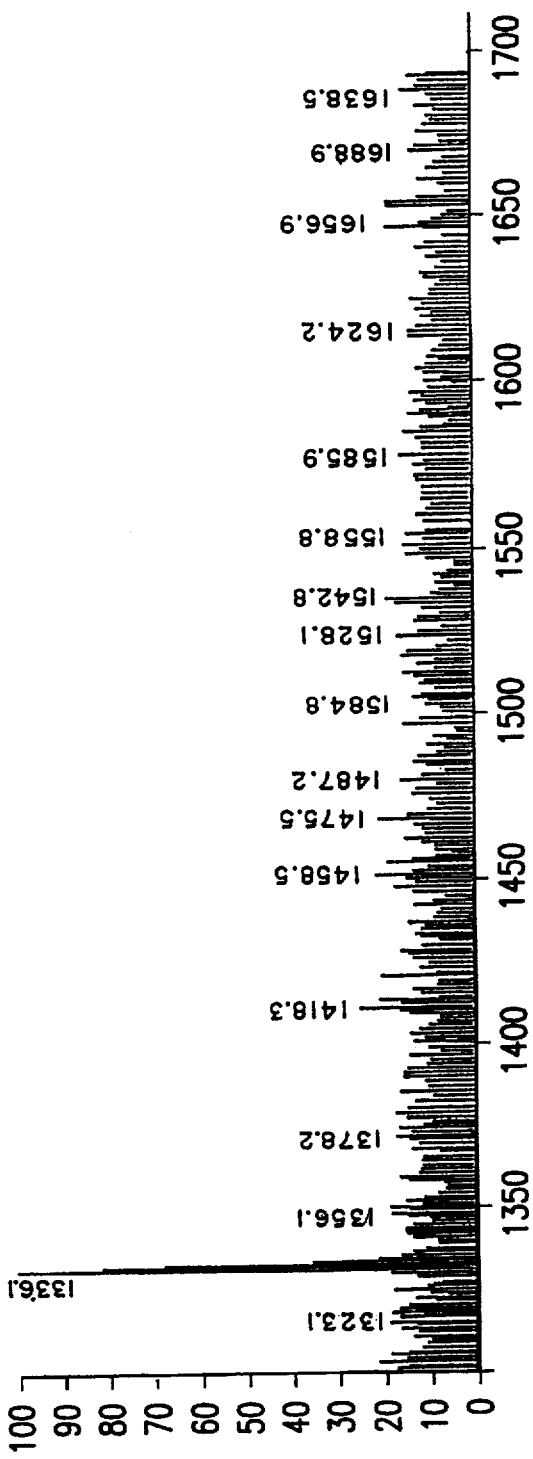
Figure 22:
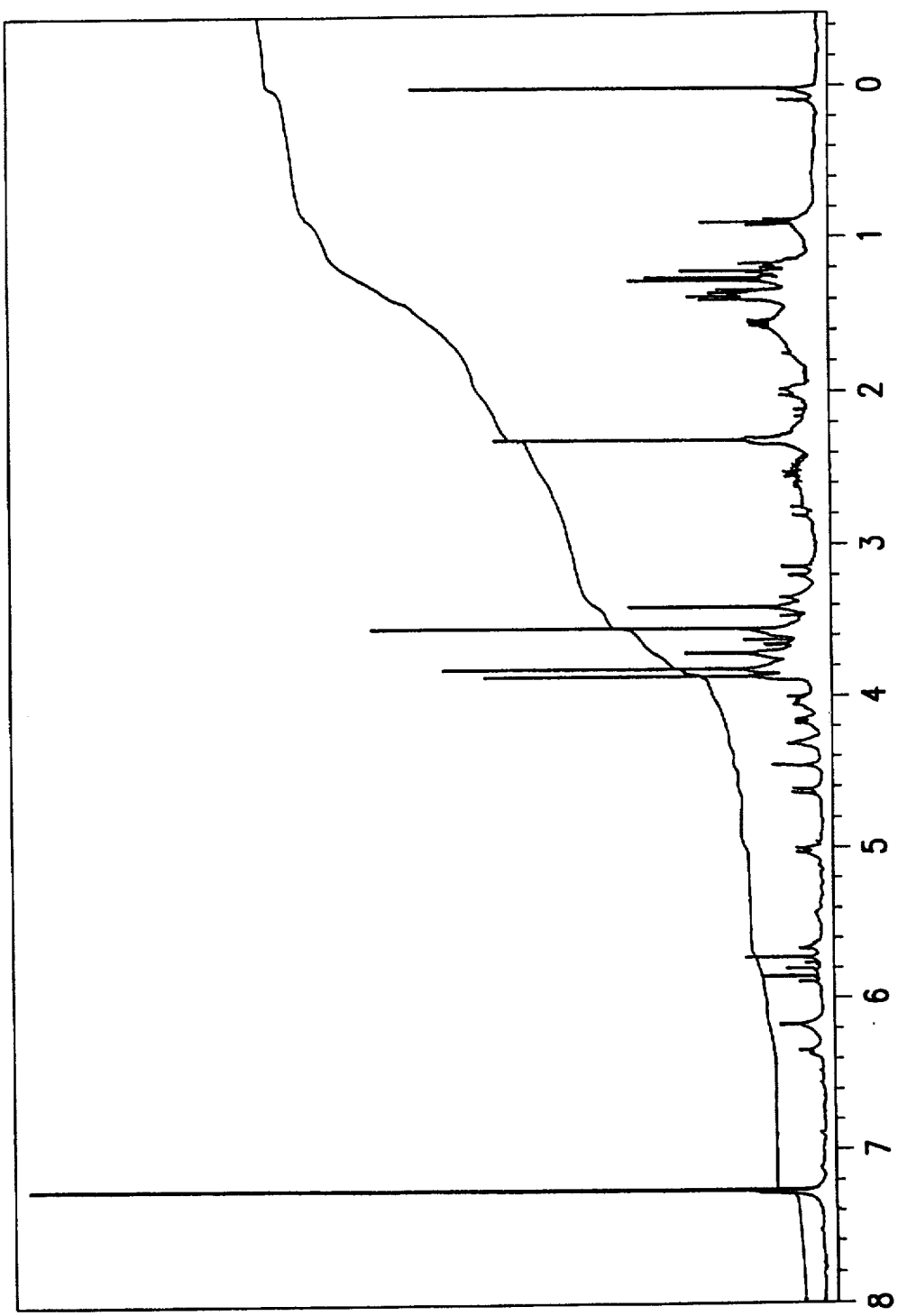
Figure 23A:
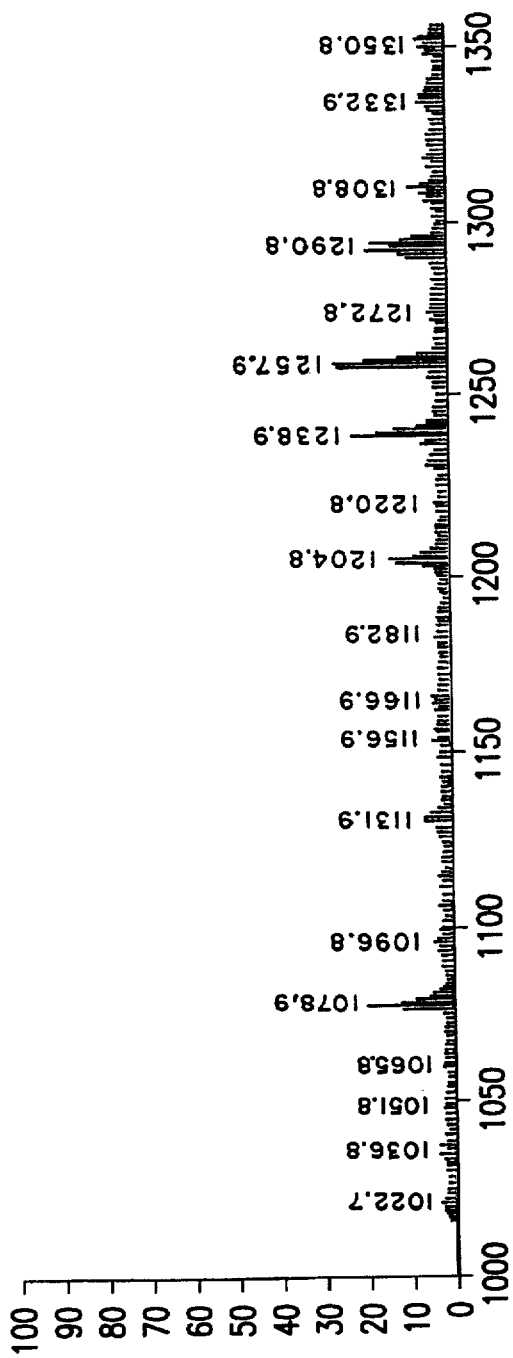
Figure 23B:
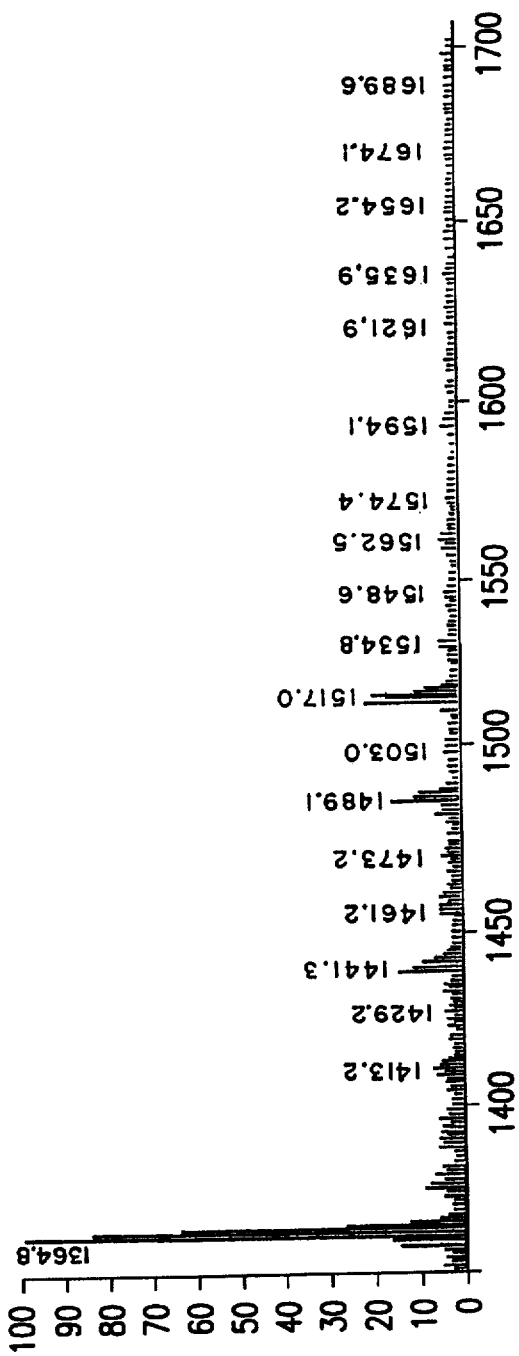

FIG. III is the infrared spectrum of LL-E33288$\gamma_1'$.

FIG. IV is the proton magnetic resonance spectrum of LL-E33288$\alpha_2'$.

FIG. V is the carbon-13 nuclear magnetic resonance spectrum of LL-E33288$\alpha_2'$.

FIG. VI is the ultraviolet spectrum of LL-E33288$\alpha_3'$.

FIG. VII is the infrared spectrum of LL-E33288$\alpha_3'$.

FIG. VIII is the proton magnetic resonance spectrum of LL-E33288$\alpha_3$.

FIG. IX is the carbon-13 nuclear magnetic resonance spectrum of LL-E33288$\alpha_3'$.

FIG. X is the ultraviolet spectrum of N-acetyl LL-E33288$\gamma_1'$.

FIG. XI is the infrared spectrum of N-acetyl LL-E33288$\gamma_1'$.

FIG. XII is the proton magnetic resonance spectrum of N-acetyl LL-E33288$\gamma_1'$.

FIG. XIII is the carbon-13 nuclear magnetic resonance spectrum of N-acetyl LL-E33288$\gamma_1'$.

FIG. XIV is the ultraviolet spectrum of iodo LL-E33288 pseudoaglycone.

FIG. XV is the infrared spectrum of iodo LL-E33288 pseudoaglycone.

FIG. XVI is the proton magnetic resonance spectrum of iodo LL-E33288 pseudoaglycone.

FIG. XVII is the carbon-13 magnetic resonance spectrum of iodo LL-E33288 pseudoaglycone.

FIG. XVIII is the ultraviolet spectrum of LL-E33288$\gamma_2'$.

FIG. XIX is the proton magnetic resonance spectrum of LL-E33288$\gamma_2'$.

FIG. XX is the infrared spectrum of LL-E33288$\gamma_2'$.

FIG. XXI is the mass spectrum of LL-E33288$\gamma_2'$.

FIG. XXII is the proton magnetic resonance spectrum of the propyl disulfide of LL-E33288$\gamma_1'$.

FIG. XXIII is the mass spectrum of the propyl disulfide of LL-E33288$\gamma_1'$.

DETAILED DESCRIPTION

As background, the family of antibacterial and antitumor agents, known collectively as the LL-E33288 complex are described and claimed in copending U.S. Pat. No. 4,970,198 (1990) and are used to prepare some of the disulfur antitumor agents of our invention. The application describes the LL-E33288 complex, the components thereof, namely, LL-E33288$\alpha_1$-Br, LL-E33288$\alpha_1$-I, LL-E33288$\alpha_2$-Br, LL-E33288$\alpha_2$-I, LL-E33288$\alpha_3$-Br, LL-E33288$\alpha_3$-I, LL-E33288$\alpha_4$-Br, LL-E33288$\beta_1$-Br, LL-E33288$\beta_1$-I, LL-E33288$\beta_2$-Br, LL-E33288$\beta_2$-I, LL-E33288$\gamma_1$-Br, LL-E33288$\gamma_1$-I, and LL-E33288$\delta_1$-I, and methods for their production by aerobic fermentation utilizing a new strain of *Micromonospora echinospora* ssp calichensis or natural or derived mutants thereof. Ser. No. 009,321 also discloses proposed structures for some of the above named components. Representative proposed structures are reproduced in Table I, below, wherein W is the remainder of the molecule attached to $CH_3SSS-$.

Additional members of the LL-E33288 complex are described and claimed in copending U.S. Pat. No. 4,934,244 (1990) and are likewise useful for preparing the targeted forms of the antitumor agents of our invention. This application describes the LL-E33288 bromo- and iodo-pseudoaglycones of the series, which have been prepared by chemical means. The application also describes dihydro derivatives accessible from all the above-named antitumor antibiotics through sodium borohydride reduction of the ketone at $C_{11}$ to a hydroxyl group. These latter proposed structures are reproduced in Table II.

Still other members of the LL-E33288 family of antitumor antibiotics are described and claimed in our U.S. Pat. No. 5,079,233 (1992), and also are useful for preparing additional targeted forms of the antitumor agents of our invention. This application describes N-acyl derivatives of several members of the LL-E33288 complex which have been prepared by chemical means. These proposed structures are likewise reproduced in Table II.

TABLE I

Proposed Structures for $CH_3-SSS-W$ isolated from natural sources (wherein W is the substituent attached to $CH_3-SSS-$ below)

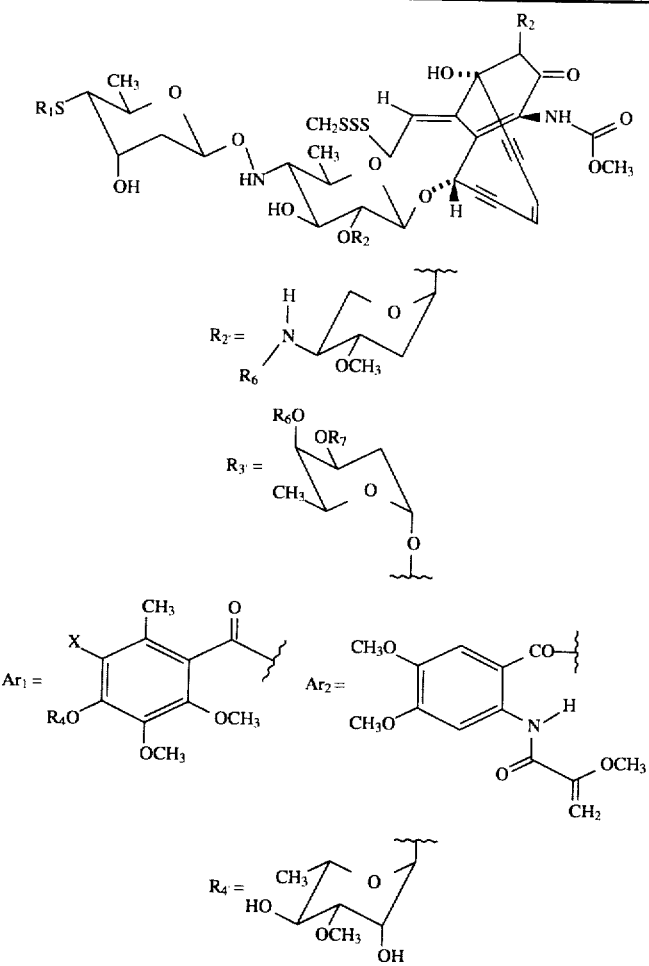

| Designation | $R_1$ | $R_2$ | $R_3$ | $R_4$ | $R_5$ | $R_6$ | $R_7$ | X |
|---|---|---|---|---|---|---|---|---|
| E33288$\alpha_2^I$ | $Ar_1$ | $R_{2'}$ | H | H | $C_2H_5$ | | | I |
| E33288$\alpha_3^I$ | $Ar_1$ | H | H | $R_{4'}$ | | | | I |
| E33288$\beta_1^I$ | $Ar_1$ | $R_{2'}$ | H | $R_{4'}$ | $(CH_3)_2CH$ | | | I |
| E33288$\gamma_1^I$ | $Ar_1$ | $R_{2'}$ | H | $R_{4'}$ | $C_2H_5$ | | | I |
| E33288$\delta_1^I$ | $Ar_1$ | $R_{2'}$ | H | $R_{4'}$ | $CH_3$ | | | I |
| E33288$\beta_1^{Br}$ | $Ar_1$ | $R_{2'}$ | H | $R_{4'}$ | $(CH_3)_2CH$ | | | Br |
| E33288$\gamma_1^{Br}$ | $Ar_1$ | $R_{2'}$ | H | $R_{4'}$ | $C_2H_5$ | | | Br |
| E33288$\alpha_2^{Br}$ | $Ar_1$ | $R_{2'}$ | H | H | $C_2H_5$ | | | Br |
| E33288$\alpha_3^{Br}$ | $Ar_1$ | H | H | $R_{4'}$ | | | | Br |
| Esperamicin $A_1$ | $CH_3$ | $R_{2'}$ | $R_{3'}$ | | $(CH_3)_2CH$ | H | $Ar_2$ | |
| Esperamicin $A_2$ | $CH_3$ | $R_{2'}$ | $R_{3'}$ | | $(CH_3)_2CH$ | $Ar_2$ | H | |
| Esperamicin $A_{1b}$ | $CH_3$ | $R_{2'}$ | $R_{3'}$ | | $CH_3CH_2$ | H | $Ar_2$ | |

TABLE II

Proposed Structures for $CH_3-SSS-W$ derived from chemical manipulation of the compounds of Table I (wherein W is the substituent attached to $CH_3-SSS-$ below)

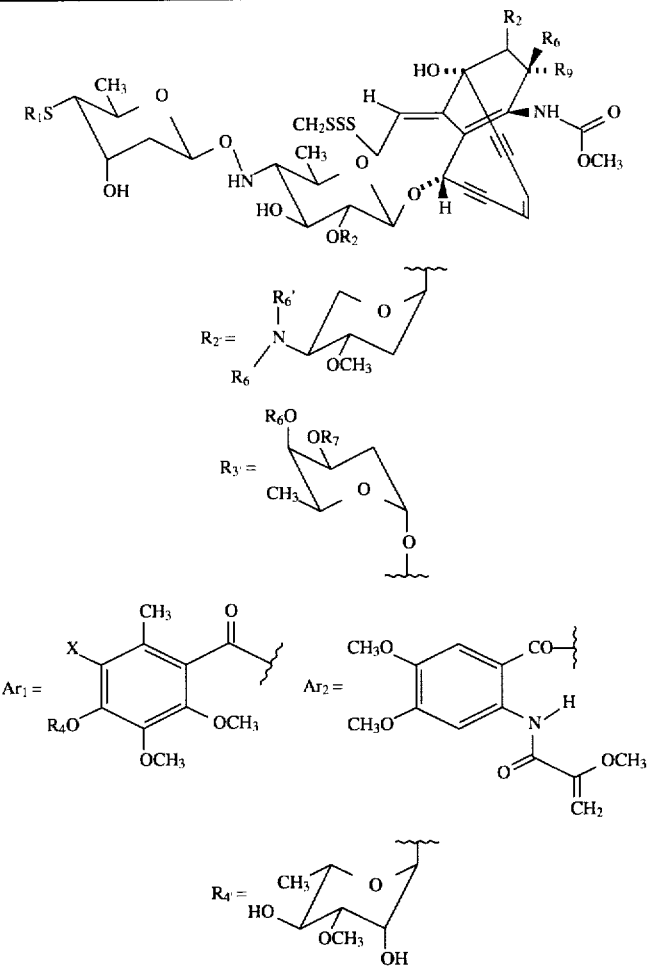

| Designation | $R_1$ | $R_2$ | $R_3$ | $R_4$ | $R_5$ | $R_{5'}$ | $R_6$ | $R_7$ | $R_8$ | $R_9$ | X |
|---|---|---|---|---|---|---|---|---|---|---|---|
| Dihydro LL-E33288$\alpha_2^I$ | $Ar_1$ | $R_{2'}$ | H | H | $C_2H_5$ | H | | | OH | H | I |
| N-Acyl LL-E33288$\alpha_2^I$ | $Ar_1$ | $R_{2'}$ | H | H | $C_2H_5$ | RCO | | | =O | | I |
| Dihydro LL-E33288$\alpha_3^I$ | $Ar_1$ | H | H | $R_{4'}$ | | | | | OH | H | I |
| Dihydro LL-E33288$\beta_1^I$ | $Ar_1$ | $R_{2'}$ | H | $R_{4'}$ | $(CH_3)_2CH$ | H | | | OH | H | I |
| N-Acyl LL-E33288$\beta_1^I$ | $Ar_1$ | $R_{2'}$ | H | $R_{4'}$ | $(CH_3)_2CH$ | RCO | | | =O | | I |
| Dihydro LL-E33288$\gamma_1^I$ | $Ar_1$ | $R_{2'}$ | H | $R_{4'}$ | $C_2H_5$ | H | | | OH | H | I |
| N-Acyl LL-E33288$\gamma_1^I$ | $Ar_1$ | $R_{2'}$ | H | $R_{4'}$ | $C_2H_5$ | RCO | | | =O | | I |
| Dihydro LL-E33288$\delta_1^I$ | $Ar_1$ | $R_{2'}$ | H | $R_{4'}$ | $CH_3$ | H | | | OH | H | I |
| N-Acyl LL-E33288$\delta_1^I$ | $Ar_1$ | $R_{2'}$ | H | $R_{4'}$ | $CH_3$ | RCO | | | =O | | I |
| Iodo LL-E33288 pseudoaglycone | $Ar_1$ | H | H | H | | | | | =O | | I |
| Dihydro-Iodo LL-E33288 pseudoaglycone | $Ar_1$ | H | H | H | | | | | OH | H | I |
| Dihydro LL-E33288$\beta_1^{Br}$ | $Ar_1$ | $R_{2'}$ | H | $R_{4'}$ | $(CH_3)_2CH$ | H | | | OH | H | Br |
| N-Acyl LL-E33288$\beta_1^{Br}$ | $Ar_1$ | $R_{2'}$ | H | $R_{4'}$ | $(CH_3)_2CH$ | RCO | | | =O | | Br |
| Dihydro LL-E33288$\gamma_1^{Br}$ | $Ar_1$ | $R_{2'}$ | H | $R_{4'}$ | $C_2H_5$ | H | | | OH | H | Br |
| N-Acyl LL-E33288$\gamma_1^{Br}$ | $Ar_1$ | $R_{2'}$ | H | $R_{4'}$ | $C_2H_5$ | RCO | | | =O | | Br |
| Dihydro LL-E33288$\alpha_2^{Br}$ | $Ar_1$ | $R_{2'}$ | H | H | $C_2H_5$ | H | | | OH | H | Br |
| N-Acyl LL-E33288$\alpha_2^{Br}$ | $Ar_1$ | $R_{2'}$ | H | H | $C_2H_5$ | RCO | | | =O | | Br |
| Dihydro LL-E33288$\alpha_3^{Br}$ | $Ar_1$ | H | H | $R_{4'}$ | | | | | OH | H | Br |
| Bromo LL-E33288 pseudoaglycone | $Ar_1$ | H | H | H | | | | | =O | | Br |
| Dihydro-bromo LL-E33288 pseudoaglycone | $Ar_1$ | H | H | H | | | | | OH | H | Br |

TABLE II-continued

Proposed Structures for $CH_3-SSS-W$ derived from chemical manipulation of the compounds of Table I (wherein W is the substituent attached to $CH_3-SSS-$below)

| N-Acyl Esperamicin $A_1$ | $CH_3$ | $R_2·$ | $R_3·$ | $(CH_3)_2CH$ | $CH_3CO$ | H | $Ar_2$ |
| N-Acyl Esperamicin $A_2$ | $CH_3$ | $R_2·$ | $R_3·$ | $(CH_3)_2CH$ | $CH_3CO$ | $Ar_2$ | H |
| N-Acyl Esperamicin $A_{1b}$ | $CH_3$ | $R_2·$ | $R_3·$ | $CH_3CH_2$ | $CH_3CO$ | H | $Ar_2$ |

R = hydrogen or a branched or unbranched alkyl $(C_1-C_{10})$ or alkylene $(C_1-C_{10})$ group, an aryl or heteroaryl group, or an aryl-alkyl $(C_1-C_6)$ or heteroaryl-alkyl $(C_1-C_6)$ group, all optionally substituented by one or more hydroxy, amino, carboxy, halo, nitro, lower $(C_1-C_3)$ alkoxy, or lower $(C_1-C_6)$ thioalkoxy groups.

Disulfur compounds of the invention are also prepared from certain other antibiotics, namely:

1) Esperamicin BBM-1675, a novel class of potent antitumor antibiotics. I. Physico-chemical data and partial structure. M. Konishi, et. al., J. Antibiotics, 38, 1605 (1985). A new antitumor antibiotic complex. M. Konishi, et. al., U.K. Patent Application GB 2,141,425A, May 15, 1984.
2) New antitumor antibiotics, FR-900405 and FR-900406.I. Taxonomy of the producing strain. M. Iwami, et. al., J. Antibiotics 38, 835 (1985). New antitumor antibiotics FR-900405 and FR-900406.II. Production, isolation, characterization and antitumor activity. S. Kiyoto, et. al., J. Antibiotics, 38, 340 (1985).
3) PD114759 and PD115028, novel antitumor antibiotics with phenomenal potency. I. Isolation and characterization. R. H. Bunge, et. al., J. Antibiotics, 37, 1566 (1984). Biological and biochemical activities of the novel antitumor antibiotic PD114759 and related derivatives. D. W. Fry et. al., Investigational New Drugs, 4, 3 (1986).
4) New Antibiotic complex CL-1577A, CL-1577B produced by Streptomyces sp. ATCC 39363. European Patent Application 0,132,082, A2.
5) CL-1577D and CL-1577E Antibiotic antitumor compounds, their production and use. U.S. Pat. No. 4,539,203.
6) CL-1724 Antibiotic compounds, their production and use. U.S. Pat. No. 4,554,162.
7) New antitumor antibiotics BBM-1675-A3 and BBM-1675-A4, obtained by fermentation of *actinomadura verrucosospora* strains H964-92 (ATCC 39334) or A1327Y (ATCC 39638). U.S. Pat. No. 4,675,187.
8) New N-acetyl-esperamicin $A_1$, $A_2$ and $A_{1b}$ derivatives with antimicrobial and antitumor activities. European Patent 289,030.

All of the information regarding BBM-1675, FR-900405, FR-900406, PD114759, PD115028, CL-1577A, CL-1577B, CL-1577D, CL-1577E and CL-1724 contained in the above citations is incorporated herein by reference. The complete structures of esperamicins $A_1$, $A_2$ and $A_{1b}$ (the BBM-1675 complex) and their respective N-acetyl derivatives have been reported, and these are included in Tables I and II. The physical characteristics of the other above-named antitumor antibiotics indicate that they all are identical or very similar in structure to the esperamicins, and all contain a methyltrithio functional group.

As can be seen from the structures disclosed in Tables I and II, the $\alpha_1$, $\alpha_2$, $\alpha_3$, $\alpha_4$, $\beta_1$, $\beta_2$, $\gamma_1$, $\delta$ and pseudoaglycone components of the LL-E33288 complex and their derivatives, as well as the BBM-1675, FR-900405, FR-900406, PD114759, PD115028, CL-1577A, CL-1577B, CL-1577D, CL-1577E and CL-1724 antibiotics and their derivatives each contain a methyltrithio group in their structures.

It has now been discovered that the reaction of any of the above cited antibiotics with an unsubstituted or substituted alkyl or aryl mercaptan results in displacement of the methyl perthiolate anion from the trisulfide moiety resulting in the formation of a stable disulfide (Scheme I), below.

Scheme I

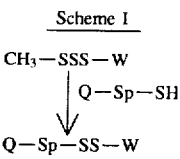

The compounds of Tables I and II are transformed with thiol-containing organic molecules according to Scheme I to produce new compositions useful as antibacterial and anticancer agents in their own right, wherein W, R, $R_1$, $R_2$, $R_3$, $R_4$, $R_5$, $R_6$, $R_7$, $R_8$, $R_9$, $R_2'$, $R_3'$, $R_4'$, $R_5'$, $Ar_1$, $Ar_2$ and X are as hereinbefore defined in Tables I and II, Sp is straight or branched-chain divalent or trivalent $(C_1-C_{18})$ radicals, divalent or trivalent aryl or heteroaryl radicals, divalent or trivalent $(C_3-C_{18})$ cycloalkyl or heterocycloalkyl radicals, divalent or trivalent aryl- or heteroarylalkyl $(C_1-C_{18})$ radicals, divalent or trivalent cycloalkyl- or heterocycloalkyl-alkyl $(C_1-C_{18})$ radicals, or divalent or trivalent $(C_2-C_{18})$ unsaturated alkyl radicals, wherein if Sp is a trivalent radical, it can be additionally substituted by amino, alkylamino, arylamino, heteroarylamino carboxyl, lower alkoxy, hydroxy, thiol, or lower alkylthio groups; Q is hydrogen, halogen, amino, alkylamino, dialkylamino, arylamino, heteroarylamino, piperidino, pyrrolidino, piperazino, carboxyl, carboxaldehyde, lower alkoxy, hydroxy, thiol, lower alkyldicarboxyl, or a group chosen from the following: —$CONHNH_2$, —$NHCONHNH_2$, $NHCSNHNH_2$, or —$ONH_2$; with the proviso that when Sp is ethylidene, Q cannot be hydrogen.

As a preferred embodiment of this invention, disulfides of the formula Q—Sp—SS—W are prepared from the antitumor antibiotics designated LL-E33288 ($CH_3SSS$—W) wherein:

W is

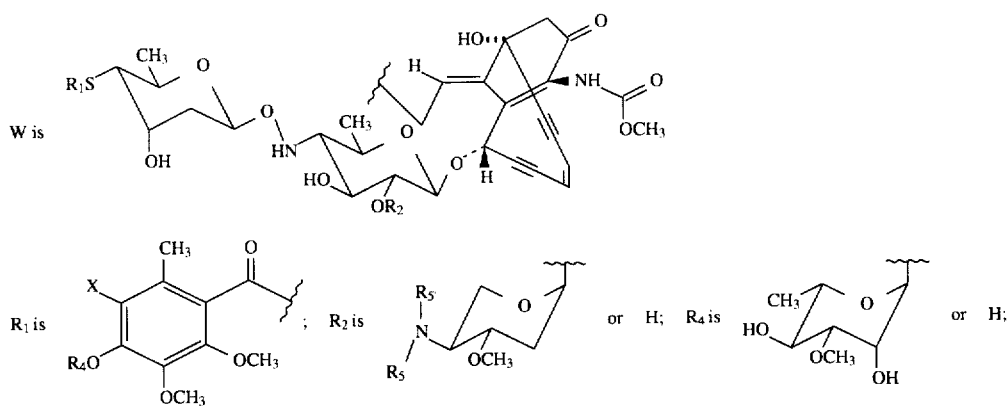

$R_5$ is $CH_3$, $C_2H_5$, or $(CH_3)_2CH$; X is an iodine or bromine atom; $R_{5'}$ is a hydrogen or the group RCO, wherein R is hydrogen, $CH_3$, or a mono-substituted aryl group; and Sp and Q are as hereinbefore defined.

As an example, reaction of LL-E33288$\gamma_1$-I with methyl mercaptan in acetonitrile produces LL-E33288$\gamma_2$-I, a new antitumor compound, which is also produced by the aerobic fermentation conditions described in the above-cited patent applications.

The above reaction is not limited to the iodo derivatives of the LL-E33288 antibiotics. If, for example, LL-E33288$\gamma_1$-Br is used, the product will be LL-E33288$\gamma_2$-Br and in fact the alkyl disulfide bromo of any E33288-bromo antibiotic will be realized under similar conditions.

The proposed structure of the two aforementioned antibiotics after reaction with methyl mercaptan are given below.

which additionally contain a chromophoric unit that absorbs or emits light in areas of the electromagnetic spectrum not obscured by cellular chromophores, useful biochemical tools for studying double strand DNA breaks and cellular localization of this class of compounds can be generated. Similarly, the introduction of radiolabels by this reaction is within the scope of our invention. Thus, for example, when E-33288$\gamma_1$-I is reacted with 7-(2-thioethylamino)-4-methyl-coumarin, a derivative is obtained which fluoresces intensely upon irradiation with ultraviolet light, permitting location of the compound within cellular compartments.

In this embodiment of this invention, the compounds of Tables I and II are transformed with thiol-containing organic

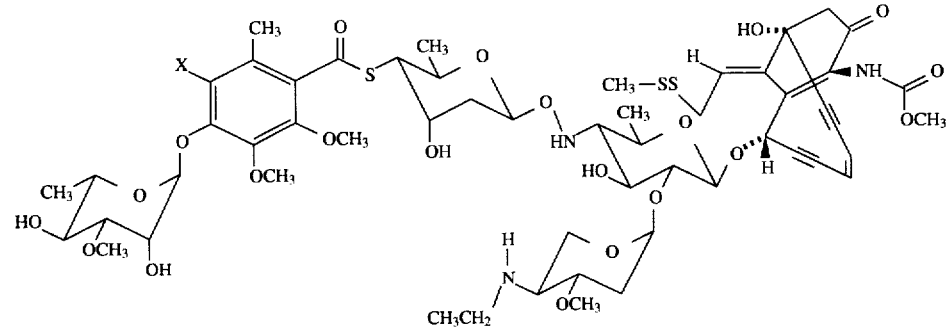

$R = CH_3, X = I = LL33288_{\gamma 2}{}^I$
$R = CH_3, X = Br = LL33288_{\gamma 2}{}^{Br}$ The transformation to the disulfur is by no means restricted to reactions of the compounds listed in Tables I and II with methyl mercaptan, but can be used with a large variety of thiol-containing organic molecules to yield novel antitumor and antibacterial agents. Moreover, the products from the reaction themselves are amenable to further transformations within the newly-introduced side-chain to produce still more novel compounds with biological activities.

The compounds of this invention in addition to their use as antitumor and antibacterial agents, are useful for assessing new modes of anticancer activity at a cellular level. The naturally-derived antibiotics described by the above-named applications and patents do not contain sufficiently strong chromophoric units such that their intracellular localization can be adequately delineated. When the native trithiomethyl derivatives are reacted with thiol-containing molecules molecules according to Scheme I to produce new compositions additionally useful as molecular probes, wherein W, R, $R_1$, $R_2$, $R_3$, $R_4$, $R_5$, $R_6$, $R_7$, $R_8$, $R_9$, $R_2'$, $R_3'$, $R_4'$, $R_5'$, $Ar_1$, $Ar_2$ and X are as hereinbefore defined in Tables I and II, Sp is straight or branched-chain divalent ($C_1$–$C_{18}$) radicals, divalent aryl or heteroaryl radicals, divalent ($C_3$–$C_{18}$) cycloalkyl or heterocycloalkyl radicals, divalent aryl or heteroaryl-alkyl ($C_1$–$C_{18}$) radicals, divalent cycloalkyl or heterocycloalkyl-alkyl ($C_1$–$C_{18}$) radicals, and divalent ($C_2$–$C_{18}$) unsaturated alkyl radicals; Q is unsubstituted or substituted fluorescing nuclei of dibenzooxazine, rhodamine, carbostyril, coumarin, fluorecein, or acridine, or a substituent containing a $^3H$ $^{14}C$ $^{35}S$, or $^{32}P$ radiolabel as part of its structure.

The compounds of this invention are active as antibacterial agents. Their in vitro antibacterial activity was determined against a spectrum of gram-positive and gram-negative bacteria by a standard agar dilution method. Mueller-Hinton agar containing two-fold decreasing concentrations of the antibiotics was poured into petri dishes. The agar surfaces were inoculated with 1 to $5\times10^4$ colony forming units of bacteria by means of a Steers replicating device. The lowest concentration of compound that inhibited growth of a bacterial strain after about 18 hours of incubation at approximately 36° C. was recorded as the minimal inhibitory concentration (MIC) for that strain. The results are summarized in Table III.

The animals used were $BDF_1$ female mice. There were 5 or 6 mice per test group. The tumor transplant was by intraperitoneal injection of 0.5 ml of dilute ascitic fluid containing $1\times10^6$ cells of lymphocytic leukemia P388 on day zero. The test compounds were administered intraperitoneally at a volume of 0.5 ml in sterile, pyrogen free saline on days 1, 5 and 9 (relative to tumor inoculation) at the indicated doses. The mice were weighed and survivors recorded on a regular basis for 30 days. The median survival time and the ratio of survival time for treated (T)/control (C) animals were calculated. Values of T/C greater than or equal to 125 are considered to reflect significant antitumor activity. The results appear in Table IV.

TABLE III

In vitro Antibacterial Activity

Minimal Inhibitory Concentration (mcg/ml)

| Organism | | LL-E33288$\gamma_2$-I | p-nitro phenyl ester of LL-E33288$\gamma_2$-I |
|---|---|---|---|
| Escherichia coli | CMC 84-11 | 0.25 | 0.5 |
| Escherichia coli | No. 311 | 0.25 | 0.5 |
| Escherichia coli | ATCC 25922 | 0.12 | 0.5 |
| Klebsiella pneumoniae | CMC 84-5 | 0.25 | 1 |
| Klebsiella pneumoniae | AD (MP) | 0.12 | 0.25 |
| Enterobacter cloacae | CMC 84-4 | 0.5 | 2 |
| Enterobacter aerogenes | IO 83-44 | 0.5 | 1 |
| Serratia marcescens | CMC 83-27 | 0.25 | 1 |
| Serratia marcescens | F-35 (MP) | 0.25 | 1 |
| Morganella morganii | IO 83-18 | 0.5 | 2 |
| Providencia stuartii | CMC 83-82 | 1 | 2 |
| Citrobacter diversus | K 82-84 | 0.5 | 1 |
| Citrobacter freundii | IO 83-13 | 0.5 | 0.5 |
| Acinetobacter sp. | CMC 83-89 | 0.25 | 0.5 |
| Acinetobacter sp. | IO 83-49 | 0.25 | 1 |
| Pseudomonas aeruginosa | 12-4-4 (MP) | 0.25 | 1 |
| Pseudomonas aeruginosa | ATCC 27853 | 0.12 | 0.5 |
| Staphylococcus aureus | Smith | 0.001 | 0.002 |
| Staphylococcus aureus | SCC 82-21 | 0.0005 | 0.004 |
| Staphylococcus aureus | ATCC 25923 | 0.0005 | 0.004 |
| Staphylococcus aureus | ATCC 29213 | 0.001 | 0.004 |
| Staphylococcus aureus | SSC 82-23 | 0.001 | 0.002 |
| Staphylococcus aureus | VGH 84-41 | 0.001 | 0.002 |
| Staphylococcus aureus | VGH 84-47 | 0.001 | 0.004 |
| Staphylococcus epidermidis | CMC 83-133 | 0.001 | 0.002 |
| Staphylococcus epidermidis | ATCC 12228 | 0.001 | 0.004 |
| Streptococcus faecalis | ATCC 29212 | 0.002 | 0.004 |
| Streptococcus faecalis | VGH 84-65 | 0.004 | 0.004 |
| Streptococcus faecalis | CMC 83-53 | 0.004 | 0.004 |
| Streptococcus faecalis | UCI 85-20 | 0.002 | 0.004 |
| Streptococcus faecalis | IO 83-28 | 0.004 | 0.004 |

The disulfide compounds described above are active antitumor agents.

Certain in vivo testing systems and protocols have been developed by the National Cancer Institute for testing compounds to determine their suitability as antineoplastic agents. These have been reported in "Cancer Chemotherapy Reports", Part III, Vol. 3, No. 2 (1972), Geran, et. al. These protocols have established standardized screening tests which are generally followed in the field of testing for antitumor agents. Of these systems, lymphocytic leukemia P388, melanotic melanoma B16, L1210 leukemia and colon 26 adenocarcinoma are particularly significant to the present invention. These neoplasms are utilized for testing as transplantable tumors in mice. Generally, significant antitumor activity, shown in these protocols by a percentage increase of mean survival times of the treated animals (T) over the control animals (C) is indicative of similar results in human leukemias and solid tumors.

Lymphocytic Leukemia P388 Test

TABLE IV

Lymphocytic Leukemia P388 Test

| Compound | Dose (mg/kg) | Median Survival (Days) | T/C × 100 % |
|---|---|---|---|
| LL-E33288$q_2$-I (Methyldisulfide of LL-E33288$\gamma_1$-I, from Example 1) | 0.02 | 19.5 | 177 |
| | 0.0125 | 21 | 191 |
| | 0.01 | 19 | 173 |
| | 0.0063 | 26 | 236 |
| | 0.005 | 21 | 191 |
| | 0.003 | 20.5 | 178 |
| | 0.0025 | 18.5 | 168 |
| | 0.0015 | 17 | 154 |
| | 0.00125 | 15.5 | 141 |
| Control | — | 11.0 | — |
| Propyldisulfide | 0.01 | 27.5 | 250 |

TABLE IV-continued

Lymphocytic Leukemia P388 Test

| Compound | Dose (mg/kg) | Median Survival (Days) | T/C × 100 % |
|---|---|---|---|
| of LL-E33288γ₁-I | 0.005 | 21.5 | 195 |
| (from Example 3) | 0.0025 | 16 | 145 |
|  | 0.00125 | 14.5 | 131 |
| Control | — | 11.0 | — |
| Propionic acid disulfide | 0.005 |  | 145 |
| of LL-E33288γ₁-I | 0.0025 |  | 125 |
| (from Example 7) |  |  |  |
| 4-Nitrophenyl propionic | 0.010 |  | 135 |
| acid ester disulfide | 0.005 |  | 185 |
| of LL-E33288γ₁-I | 0.0025 |  | 150 |
| (from Example 8) | 0.00125 |  | 130 |
| 7-(2-Mercaptoethylamino) | 0.010 | 24.5 | 223 |
| -4-methyl coumarin disulfide | 0.005 | 28.5 | 259 |
| of LL-E33288γ₁-I | 0.0025 | 26.0 | 236 |
| (from Example 9) | 0.00125 | 21.0 | 191 |
|  | 0.0006 | 18.5 | 168 |
|  | 0.0003 | 16.5 | 150 |
| Control | — | 11.0 | — |
| 3-Mercaptopropionyl | 0.005 | 18.0 | 164 |
| hydrazide disulfide | 0.0025 | 25.0 | 186 |
| of LL-E33288γ₁-I | 0.00125 | 19.0 | 173 |
| (from Example 10) | 0.0006 | 15.5 | 141 |
| Control | — | 11.0 | — |
| 3-Mercaptopropionyl | 0.040 | 15.0 | 136 |
| hydrazide disulfide | 0.020 |  | 123 |
| of LL-E33288α₁-I |  |  |  |
| (from Example 12) |  |  |  |
| Control | — | 11.0 | — |
| 3-Mercaptopropionyl | 0.080 | 21.0 | 175 |
| hydrazide disulfide | 0.040 | 18.0 | 150 |
| of N-acetyl LL-E33288γ₁-I | 0.020 | 15.0 | 125 |
| (from Example 13) |  |  |  |
| Control | — | 12.0 | — |
| 3-Mercaptopropionyl | 0.010 | 26.5 | 230 |
| hydrazide disulfide | 0.005 | 21.0 | 183 |
| of LL-E33288α₁-I | 0.0025 | 18.5 | 161 |
| (from Example 14) | 0.00125 | 18.5 | 161 |
| Control | — | 11.5 | — |
| 3-Mercaptopropionyl | 0.005 | 28.5 | 190 |
| hydrazide disulfide | 0.0025 | 23.0 | 153 |
| of LL-E33288γ₁-I | 0.00125 | 21.0 | 140 |
| (from Example 16) | 0.0006 | 19.5 | 130 |
| Control | — | 15.0 | — |
| 3-Mercaptoisovaleryl | 0.010 | 26.5 | 252 |
| hydrazide disulfide | 0.005 | 18.0 | 171 |
| of LL-E33288γ₁-I | 0.0025 | 17.0 | 162 |
| (from Example 17) | 0.00125 | 16.0 | 152 |
|  | 0.0006 | 13.0 | 124 |
|  | 0.0003 | 14.0 | 133 |
| Control | — | 10.5 | — |
| 4-Mercaptodihydrocinnamyl | 0.005 | 24.0 | 200 |
| hydrazide disulfide | 0.0025 | 28.0 | 233 |
| of LL-E33288γ₁-I | 0.00125 | 25.5 | 213 |
| (from Example 18) | 0.0006 | 18.5 | 154 |
|  | 0.0003 | 17.5 | 146 |
| Control | — | 12.0 | — |

Melanotic Melanoma B16 Test

The animals used were BDF1 female mice. There were 5 or 6 mice per test group. A one gram portion of melanotic melanoma B16 tumor was homogenized in 10 ml of cold balanced salt solution and a 0.5 ml aliquot of the homogenate was implanted intraperitoneally into each of the test mice. The test compounds were administered intraperitoneally on days 1 through 9 (relative to tumor inoculation) at the indicated doses. The mice were weighed and survivors recorded on a regular basis for 60 days. The median survival time and the ratio of survival time for treated (T)/control (C) animals were calculated. A value of T/C of greater or equal to 125 is considered indicative of significant antitumor activity. The results appear in Table V.

TABLE V

Melanotic Melanoma B16 Test

| Compound | Dose (mg/kg) | Median Survival (Days) | T/C × 100 (%) |
|---|---|---|---|
| LL-E33288γ₁-I | 0.005 | 34 | 162 |
| (methyldisulfide | 0.0025 | 38 | 181 |
| of LL-E33288γ₁-I) | 0.00125 | 33.5 | 160 |
|  | 0.0006 | 28.5 | 136 |
|  | 0.0003 | 26 | 124 |
| Control | — | 21 | — |

The invention will be further described in conjunction with the following nonlimiting examples.

EXAMPLE 1

Methyldisulfide of LL-E33288γ₁-I (LL-E33288γ₂-I)

A thiol reagent was prepared by bubbling methyl mercaptan gas into 10 ml of acetonitrile until it was essentially saturated. A 108 mg portion of LL-E33288γ₁-I was added to the thiol reagent, the resulting suspension was then vortexed to produce a solution which was placed in a −20° C. freezer overnight and then the solvent was evaporated. The residue was taken up in a small volume of ethyl acetate and this solution was dripped into 25 ml of stirred hexane giving an off-white precipitate that was dried, giving 82 mg of partially purified LL-33288γ₂-I.

The above 82 mg was treated with 0.1 ml of methanol and then 1 ml of methylene chloride was added. This solution was passed over 18 g of silica gel in a small column. The eluant used was 5% methanol in methylene chloride. The fractions were monitored by thin layer chromatography on silica gel using the system 10% isopropanol in ethyl acetate saturated with phosphate buffer. Fractions 4–11, containing LL-E33288γ₂-I were combined and evaporated. The residue was taken up in 0.5 ml of ethyl acetate and dripped into 20 ml of stirred hexane. The precipitate was collected and dried, giving 37 mg of LL-E33288γ₂-I, having ultraviolet spectra as shown in FIG. XVIII, a proton magnetic resonance spectrum as shown in FIG. XIX, an infrared spectrum as shown in FIG. XX, and a mass spectrum as shown in FIG. XXI.

EXAMPLE 2

Ethyldisulfide of LL-E33288γ-1

The reaction described in Example 1 was repeated using a thiol reagent composed of ethyl mercaptan in acetonitrile, giving the desired ethyl disulfide of LL-E33288γ₁-I.

EXAMPLE 3

Propyldisulfide of LL-E33288γ₁-I

A 60 mg portion of LL-E33288γ₁-I was dissolved in 6 ml of acetonitrile and 5 ml of a 1 μmole/ml solution of propyl mercaptan in acetonitrile was added. After 3 hours, the reaction was essentially complete and the solvent was evaporated. The residue was taken up in 3 ml of ethyl acetate, filtered and the filtrate dripped into 40 ml of stirred hexane. The precipitate was collected and dried, giving 39 mg of the propyldisulfide LL-E33288γ₁-I, having a proton magnetic resonance spectrum as shown in FIG. XXII and a mass spectrum as shown in FIG. XXIII.

EXAMPLE 4

1-Methyl-1-propyl disulfide of LL-E33288$\gamma_1$-I

A solution of 150 μg of LL-E33288$\gamma_1$-I in 1 ml of acetonitrile was treated with 50 μl of a 1 μmole/ml solution of 1-methyl-1-propyl mercaptan. After 2 hours, the reaction was complete, giving the desired 1-methyl-1-propyl disulfide of LL-E33288$\gamma_1$-I.

EXAMPLE 5 t-Butyl disulfide Analog of LL-E33288$\gamma_1$-I

A 150 μg portion of LL-E33288$\gamma_1$-I in 1 ml of acetonitrile was treated with 50 μl of a 1μ mole/ml solution of t-butyl mercaptan in acetonitrile. After 2¼ hours, the reaction was complete, giving the t-butyl disulfide of LL-E33288$\gamma_1$-I.

EXAMPLE 6 t-Butoxycarbonyl t-butyl cysteinyl disulfide of LL-E33288$\gamma_1$-I t-Butoxycarbonyl-cysteine-t-butyl ester was dissolved in acetonitrile at a concentration of 10 mg/ml. A 230 μg portion of LL-33288$\gamma_1$-I in acetonitrile was treated with 100 μl of the amino acid reagent. After 1 hour, the reaction was complete, giving the desired disulfide of LL-E33288$\gamma_1$-I.

EXAMPLE 7

3-Mercaptopropionic acid disulfide of LL-E33288$\gamma_1$-I

To a solution of 90 mg of LL-E33288$\gamma_1$-I in 90 ml of acetonitrile was added 10.6 mg of 3-mercaptopropionic acid in 1 ml of acetonitrile. The solution was vortexed and then stored at −20° C. for 6 days. The solvent was removed in vacuo and the residue chromatographed over 10 ml of silica gel in methylene chloride. The column was developed with 50 ml of methylene chloride, 50 ml of 4% methanol in methylene chloride and finally 100 ml of 8% methanol in methylene chloride. Evaporation of this last fraction gave a residue which was taken up in ethyl acetate with the aid of a little acetone and added dropwise to an excess of hexane. The precipitate was collected and dried, giving 39 mg of the desired product (FABMS, M+H 1394).

EXAMPLE 8

Reaction of LL-E33288$\gamma_1$-I with the p-nitrophenyl ester of 3-mercaptopropionic acid (A) Preparation of p-nitrophenyl ester of 3-mercaptopropionic acid Commercial 3-mercaptopropionic acid in methylene chloride containing a catalytic amount of concentrated sulfuric acid was treated with isobutylene for 20 minutes. The solution was then extracted with 1N sodium-bicarbonate solution after which the methylene chloride solution was dried using anhydrous magnesium sulfate. The solution was then evaporated to a colorless mobile liquid which NMR and mass spectral data indicated was the S-t-butyl mercaptopropionic acid, t-butyl ester.

An aliquot of this ester was refluxed with 6N hydrochloric acid in dioxane for 2.5 hours. The solvent was evaporated, ethyl acetate was added and this solution was extracted with sodium carbonate. The sodium carbonate extract was treated with 6N hydrochloric acid until the pH of the suspension was 2.0. The suspension was then extracted with ethyl acetate, the extract dried over anhydrous magnesium sulfate and the solvent evaporated to a colorless liquid which $^1$H NMR and mass spectral data indicated was S-t-butyl mercaptopropionic acid.

This compound was converted to the p-nitrophenol ester by treatment with equimolar amounts of p-nitrophenol and dicyclohexylcarbodiimide in tetrahydrofuran for 4 hours. The dicyclohexyl urea by-product was removed by filtration and the filtrate was evaporated to an oil which was purified by passage over neutral silica gel using the solvent system hexane:methylene chloride (50:50). The pure p-nitrophenyl ester derivative was a faintly yellow, mobile oil.

The free mercaptan was unmasked by the following procedure. The S-t-butyl mercaptopropionic acid p-nitrophenyl ester was dissolved in trifluoroacetic acid and a slight molar excess (10%) of mercuric acetate was added. The mixture was stirred for 30 minutes, then the trifluoroacetic acid was evaporated off and the residue taken up in dimethylformamide. This solution was treated with hydrogen sulfide gas for 15 minutes, then the black mercuric sulfide was filtered off and the filtrate evaporated under reduced pressure to eliminate up to 99% of the dimethylformamide. The resultant slightly brownish mobile liquid was purified over neutral silica gel using hexane:methylene chloride (50:50). The major component was shown by $^1$H NMR to contain a small amount of the t-butyl mercapto derivative. Analytical HPLC over two Perkin-Elmer Pecosphere $C_{18}$ columns in tandem [4.6×33 mm and 4.6×83 mm] using a gradient system of 37.5/62.5 to 47.5/52.5 of acetonitrile and 0.1M ammonium acetate buffer at pH 6.5 (acetic acid) over a 12 minute span indicated that the product was 88% of the p-nitrophenyl ester of 3-mercaptopropionic acid and 10% of the less polar S-t-butyl mercaptopropionic acid p-nitrophenyl ester. There was also a small amount of free p-nitrophenol present.

(B) Reaction of p-nitrophenyl ester of 3-mercaptopropionic acid with LL-E33288$\gamma_1$-I A 100 mg portion of LL-E33288$\gamma_1$-I was dissolved in 50 ml of acetonitrile. To this was added a solution of 25.7 mg of p-nitrophenyl ester of 3-mercaptopropionic acid in 1 ml of acetonitrile. The reaction was left at −20° C. for 48 hours. HPLC indicated the reaction was complete. The solution was evaporated to dryness and the residue taken up in 4–5 ml of ethyl acetate using sonication to effect solution. The mixture was filtered and the filtrate dripped into 45 ml of stirred hexane. The resultant faintly yellow solid was collected and dried under reduced pressure, giving 93 mg of the p-nitrophenyl ester of propionic acid derivative of LL-E33288$\gamma_2$-I as established by 1H NMR. By FABMS the [M+H] ion appeared at m/z=1515. Retention time on $C_{18}$ reverse phase HPLC:18 min. with 50% acetonitrile/0.1M aqueous ammonium acetate (LL-E33288$\gamma_1{}^I$:8.0 min., ester hydrolysis product:1.5 min.).

EXAMPLE 9

7-(2-Mercaptoethylamino)-4-methyl coumarin disulfide of LL-E33288$\gamma_1$-I

To 10 mg of 70% pure LL-E33288$\gamma_1$-I in 9 mL of acetonitrile was added 1.2 mg of 7-(2-thioethylamino)-4-methyl coumarin in 1 mL acetonitrile. After stirring for 36 hours at 0° C. the solvent was stripped and the product was chromatographed on silica gel with 5% methanol in chloroform to give 5 mg of the desired product. FABMS, m/z=1523 (M+H); retention time on a $C_{18}$ reverse phase HPLC column: 5.4 min. with 56% acetonitrile, 0.1M aqueous ammonium chloride. (LL-E33288$\gamma_1$-I retention time in the same system is 5.5 min.).

EXAMPLE 10

3-Mercaptopropionyl hydrazide disulfide of LL-E33288$\gamma_1'$

To 5.4 ml (3 eq) of anhydrous hydrazine in 100 ml of refluxing tetrahydrofuran under argon was added dropwise 9.2 ml (83 mmol) of methyl 3-mercaptopropionate in 50 ml tetrahydrofuran over 2 hours. The solution was refluxed an additional two hours, evaporated, and then diluted and evaporated twice from 300 ml of toluene. The product was applied to a plug of silica gel with 5% ethyl acetate/chloroform and eluted from the plug with 20% methanol/chloroform. The resultant 3-mercaptopropionyl hydrazide was a faintly pink oil which solidified when cooled but melted at room temperature.

To 50 mg of LL-E33288$\gamma_1'$ in 50 ml of acetonitrile at −15° C. was added 6.6 mg of 3-mercaptopropionyl hydrazide in 1 ml tetrahydrofuran. One equivalent of triethylamine or 1 equivalent of triethylamine and 1 equivalent of acetic acid was added. The reaction was allowed to stir at 0° C. for 1 hour and the solvent was then evaporated. The residue was chromatographed on silica gel with a 10–15% methanol-in-chloroform gradient to yield 26 mg of the desired product. FABMS, m/z=1408 (M+H); retention time on reverse phase $C_{18}$ HPLC: 5.0 min. in 41% acetonitrile/0.1M aqueous ammonium acetate.

EXAMPLE 11

N-[[(4-Methyl-coumarin-7-yl)amino]acetyl]cysteine hydrazide disulfide of LL-E33288$\gamma_1'$ A mixture of 1.0 g (5.7 mmol) of 4-methyl-7-aminocoumarin, 3.0 ml of ethyl bromoacetate (5 eq), 90 mg (0.1 eq) of sodium iodide, and 30 ml dimethylformamide was heated under argon at 80° C. for 5 hours. The mixture was cooled, diluted with ethyl ether, washed three times with 50% brine, dried with magnesium sulfate, and evaporated to dryness. The crude product was dissolved in chloroform containing 1% ethyl acetate and filtered through a plug of silica gel. Recrystallization from diethyl ether containing a trace of chloroform yielded pure ethyl N-[(4-methyl-coumarin-7-yl)amino]acetate.

To 1.96 g (7.5 mmol) of the above ester in 15 ml of methanol and 15 ml of tetrahydrofuran was added 10 ml of 1N aqueous sodium hydroxide. After 30 minutes, 4 ml of 10% aqueous hydrochloric acid was added. The organic solvents were evaporated and the resultant crystalline product was filtered and washed with cold ethanol and then ether. This material was dissolved in 20 ml of tetrahydrofuran and 4 ml of dimethylformamide. Dicyclohexylcarbonyldiimide (1.3 g, 2.2 eq) was added and the reaction allowed to stir for 15 minutes. Cysteine ethyl ester hydrochloride (1.6 g, 2.5 eq) and triethylamine (1.2 ml) were then added. After a further three hours, the reaction was diluted with ethyl ether containing 5% methylene chloride and washed once with 10% aqueous hydrochloric acid and twice with brine. After drying with magnesium sulfate and evaporating the solvents, the crude product was crystallized by dissolving in chloroform containing a minimal amount of ethanol and then adding an excess of ether. The crystals were filtered and dried to give pure N-[[(4-methyl-coumarin-7-yl)amino]acetyl]cysteine ethyl ester.

A mixture of 5 ml of chloroform, 20 ml of methanol, and 0.4 ml of hydrazine hydrate were heated to reflux under argon. To this was added 550 mg of N-[[(4-methyl-coumarin-7-yl)amino]acetyl]cysteine ethyl ester. After refluxing for 9 hours the mixture was cooled and the solid product was filtered and washed with chloroform and then ethyl ether. The crude product (which contained thiol and disulfide) was dissolved in dimethylformamide containing dithiothreitol and triethyl amine. After 30 minutes the product was precipitated with excess ethyl ether and collected by filtration. This material was purified further by recrystallization from degassed acetonitrile containing dithiothreitol and a trace of triethyl amine to give pure N-[[(4-methyl-coumarin-7-yl)amino]acetyl]cysteine hydrazide.

To 12 mg of LL-E33288$\gamma_1'$ in 12 ml acetonitrile at 0° C. was added 4 mg of N-[[(4-methyl-coumarin-7-yl)amino]acetyl]cysteine hydrazide in ml dimethylformamide. After stirring overnight another 2 mg of N-[[(4-methyl-coumarin-7-yl)amino]cysteine hydrazide in 0.6 ml dimethylformamide was added. The reaction was stirred for 3 days at 0° C. and filtered. The acetonitrile was evaporated and the resultant dimethylformamide solution was diluted with an excess of 1:1 hexanes/ether. The product was isolated by filtration and further purified by chromatography on silica gel with a 15–20% gradient of methanol in chloroform to yield 3 mg of the desired product. Retention time on reverse phase $C_{18}$ HPLC: 3.5 minutes using 45% acetonitrile/0.1M aqueous ammonium acetate (LL-E33288$\gamma_1'$:15.5 min. in the same system).

EXAMPLE 12

3-Mercaptopropionyl hydrazide disulfide of LL-E33288$\alpha_3'$

To 10 mg of LL-E33288$\alpha_3'$ in 10 ml of acetonitrile at −15° C. was added 6.6 mg of 3-mercaptopropionyl hydrazide in 1 mL acetonitrile. One equivalent of triethylamine or one equivalent of triethyl and one equivalent of acetic acid were added. The reaction was allowed to stir at 0° C. for 1 hour and the solvent was then evaporated. The residue was chromatographed on silica gel with a 10–15% methanol-in-chloroform gradient to give the desired product. FABMS, m/z=1251 (M+H); retention time on reverse phase $C_{18}$ HPLC:2.1 min. in the system 45% acetonitrile/0.1M aqueous ammonium acetate (LL-E33288$\alpha_3'$:5.7 min. in the same system).

EXAMPLE 13

3-Mercaptopropionyl hydrazide disulfide of N-acetyl LL-E33288$\gamma_1'$

To 10 mg of N-acetyl LL-E33288$\gamma_1'$ in 10 ml of acetonitrile at −15° C. was added 1.5 eq of 3-mercaptopropionyl hydrazide in 85 μl acetonitrile. One equivalent of triethylamine was added. The reaction was allowed to stir at 0° C. for two hours and the solvent was then evaporated. The residue was chromatographed on silica gel with a 10–15% methanol-in-chloroform gradient to yield the desired product. FABMS, m/z=1450 (M+H); retention time on $C_{18}$ reverse phase HPLC:2.5 min. with 50% acetonitrile/0.05M aqueous ammonium dihydrogen phosphate (N-acetyl LL-E33288$\gamma_1$':6.6 min. in the same system).

EXAMPLE 14

3-Mercaptopropionyl hydrazide disulfide of LL-E33288$\alpha_2$'

To 10 mg of LL-E33288$\alpha_2$' in 10 ml acetonitrile at −15° C. was added 1.5 eq of 3-mercaptopropionyl hydrazide in 1 ml of acetonitrile. One equivalent of triethylamine was added. The reaction was allowed to stir at 0° C. for one hour and the solvent was then evaporated. The residue was chromatographed on silica gel with a 5–15% methanol-in-chloroform gradient to yield the desired product. FABMS, m/z=1248 (M+H); retention time on $C_{18}$ reverse phase HPLC:2.6 min. with 58% acetonitrile/0.05M aqueous ammonium dihydrogen phosphate (LL-E33288$\alpha_2$':7.5 min. in the same system).

EXAMPLE 15

3-Mercaptopropionyl hydrazide disulfide of iodo LL-E33288 pseudoaglycone

To 10 mg of iodo LL-E33288 pseudoaglycone in 9 ml of acetonitrile at −15° C. was added 1.5 eq of 3-mercaptopropionyl hydrazide in 1 ml of acetonitrile. One equivalent of triethylamine was added as a catalyst. The reaction was allowed to stir at 0° C. for one hour and the solvent was then evaporated. The residue was chromatographed on silica gel with a 10–15% methanol-in-chloroform gradient to yield the desired product. FABMS, m/z=1091 (M+H); retention time of $C_{18}$ reverse phase HPLC:2.8 min. with 50% acetonitrile/ 0.05M aqueous ammonium dihydrogen phosphate (iodo LL-E33288 pseudoaglycone:7.9 min. in the same system).

EXAMPLE 16

3-Mercaptobutyryl hydrazide disulfide of LL-E33288$\gamma_1$'

To 17.2 g (0.2 moles) of crotonic acid was added 18 ml (0.26 moles) of thioacetic acid. This mixture was heated at reflux under argon for 6 hours. The excess thioacetic acid was removed under aspirator vacuum and the resultant oil was dissolved in 100 ml absolute ethanol containing 200 µl of concentrated sulfuric acid. This reaction was refluxed for 10 hours and then reduced in volume under aspirator vacuum. Hexanes were added and the resultant solution washed successively with two portions of saturated sodium bicarbonate and one portion of water. This solution was then dried with magnesium sulfate, filtered, and reduced in volume to an oil. This crude product was dissolved in 250 ml of methanol containing 12 ml of hydrazine and the resultant mixture was refluxed for 10 hours under argon. The reaction mixture was reduced in volume and then distilled rapidly by Kugelrohr and crystallized from a mixture of chloroform-hexanes to give 3-mercaptobutyryl hydrazide.

To 5 mg of LL-E33288$\gamma_1$' in 5 ml of acetonitrile at −15° C. was added 1.5 eq of 3-mercaptopropionyl hydrazide in 1 ml of acetonitrile. One equivalent of triethylamine was added. The reaction was allowed to stir at 0° C. for one hour and the solvent was then evaporated. The residue was chromatographed on silica gel with a 10–15% methanol-in-chloroform gradient to yield the desired product. FABMS, m/e=1422 (M+H); retention time on $C_{18}$ reverse phase HPLC:3.5 min. with 43% acetonitrile/0.05M aqueous ammonium dihydrogen phosphate (LL-E33288$\gamma_1$':13.4 min. in the same system).

EXAMPLE 17

3-Mercaptoisovaleryl hydrazide disulfide of LL-E33288$\gamma_1$'

To 10 g (0.1 moles) of 3,3-dimethyl acrylic acid was added 9 ml (0.13 moles) of thioacetic acid. This mixture was heated at reflux under argon for 6 hours. The excess thioacetic acid was removed under aspirator vacuum and the resultant oil was dissolved in 100 ml absolute ethanol containing 200 µl of concentrated sulfuric acid. This reaction was refluxed for 34 hours before adding 16 ml of hydrazine. The resultant mixture was refluxed for 24 hours under argon. The reaction mixture was reduced in volume and then dissolved in a mixture of brine and saturated sodium bicarbonate. The product was extracted with several volumes of chloroform. The combined chloroform layers were dried with magnesium sulfate, filtered and reduced in volume to an oil. This oil was purified by flash chromatography with a methanol-chloroform gradient and then crystallized from chloroform-hexanes to give 3-mercaptoisovaleryl hydrazide.

To 15 mg of LL-E33288$\gamma_1$' in 5 ml of acetonitrile at −15° C. was added 1.5 eq of 3-mercaptoisovaleryl hydrazide in 100 µl acetonitrile. One equivalent of triethylamine was added as a catalyst. The reaction was allowed to stir at ambient temperature for 3 hours and the solvent was then evaporated. The residue was chromatographed on silica gel with a 10–15% methanol-in-chloroform gradient to yield the desired product. FABMS, m/z=1436 (M+H); retention time on $C_{18}$ reverse phase HPLC:3.9 min. with 43% acetonitrile/ 0.05M aqueous ammonium dihydrogen phosphate (LL-E33288$\gamma_1$':13.4 min. in the same system).

EXAMPLE 18 p-Mercaptodihydrocinnamyl hydrazide disulfide of LL-E33288$\gamma_1$'

To 500 mg (2.75 mmol) of p-mercaptodihydrocinnamic acid was added 15 ml methanol containing one drop of concentrated sulfuric acid. This reaction was refluxed for 5 hours and then cooled to ambient temperature. Hydrazine (1.5 ml) was added and the resultant mixture was refluxed for 2 hours under argon and then stirred for 10 hours at ambient temperature. A 200 mg portion of dithiothreitol was added to reduce any disulfides present and the reaction mixture was cooled to −15° C. The resultant crystals were filtered, washed with a mixture of ether and methanol, and then dried in a vacuum oven (50°/5 microns/10 hours) to give p-mercaptodihydrocinnamyl hydrazide.

To 25 mg of LL-E33288$\gamma_1$' in 25 ml of acetonitrile at −15° C. was added 1.5 eq of p-mercaptodihydrocinnamyl hydrazide in 1 ml of acetonitrile. The reaction was allowed to stir at 0° C. for 10 hours and the solvent was then evaporated. The residue was chromatographed on silica gel with 10–15% methanol-in-chloroform gradient to yield the desired product. FABMS, m/z=1484 (M+H); retention time on $C_{18}$ reverse phase HPLC:5.4 min. with 43% acetonitrile/ 0.05M aqueous ammonium dihydrogen phosphate (LL-E33288$\gamma_1$':13.4 min. in the same system).

EXAMPLE 19

3-Mercaptoisovaleryl hydrazide disulfide of N-acetyl LL-E33288$\gamma_1'$

To 20 mg of N-acetyl LL-E33288$\gamma_1'$ in 15 ml of acetonitrile at −15° C. was added 3 eq of 3-mercaptoisovaleryl hydrazide in 6.2 ml acetonitrile. One equivalent of triethylamine was added. The reaction was allowed to stir at ambient temperature for 2 hours and the solvent was then evaporated. The residue was chromatographed on silica gel with a 10–15% methanol-in-chloroform gradient to yield the desired product. Retention time on $C_{18}$ reverse phase HPLC:2.5 min. with 50% acetonitrile/0.05M aqueous ammonium dihydrogen phosphate (N-acetyl LL-E33288$\gamma_1'$:6.6 min. in the same system).

EXAMPLE 20

3-Mercaptobutyryl hydrazide disulfide of N-acetyl LL-E33288$\gamma_1'$

To 10 mg of N-acetyl LL-E33288$\gamma_1'$ in 7.5 ml of acetonitrile at −15° C. was added 3 eq of 3-mercaptobutyryl hydrazide in 5 ml acetonitrile. One equivalent of triethylamine was added. The reaction was allowed to stir at ambient temperature for 10 hours and the solvent was then evaporated. The residue was chromatographed on silica gel with a 10–15% methanol-in-chloroform gradient to yield the desired product. Retention time on $C_{18}$ reverse phase HPLC:4.1 min. with 43% acetonitrile/0.05M aqueous ammonium dihydrogen phosphate (N-acetyl LL-E33288$\gamma_1'$:5.6 min. in the same system).

EXAMPLE 21 p-Mercaptodihydrocinnamyl hydrazide disulfide of N-acetyl LL-E33288$\gamma_1'$ To 10 mg of N-acetyl LL-E33288$\gamma_1'$ in 7.5 ml of acetonitrile at −15° C. was added 3.0 eq of p-mercaptodihydrocinnamyl hydrazide in 2.0 ml acetonitrile. One equivalent of triethylamine was added. The reaction was allowed to stir at ambient temperature for 2 hours and the solvent was then evaporated. The residue was chromatographed on silica gel with a 10–15% methanol-in-chloroform gradient to yield the desired product. Retention time on $C_{18}$ reverse phase HPLC:7.3 min. with 43% acetonitrile/0.05M aqueous ammonium dihydrogen phosphate (N-acetyl LL-E33288$\gamma_1'$:5.6 min. in the same system).

EXAMPLE 22

7-(2-Mercaptoethylamino)-4-methyl coumarin disulfide of N-acetyl LL-E33288$\gamma_1'$ To 5 mg of N-acetyl LL-E33288$\gamma_1'$ in 4 ml of acetonitrile at −15° C. was added 1.5 eq of 7-(2-mercaptoethylamino)-4-methylcoumarin in 1 ml acetonitrile. One equivalent of triethylamine was added. The reaction was allowed to stir at 0° C. for one hour and the solvent was then evaporated. The residue was chromatographed on silica gel with a 5–15% methanol-in-chloroform gradient to yield the desired product. Retention time on $C_{18}$ reverse phase HPLC:8.6 min. with 50% acetonitrile/0.05M aqueous ammonium dihydrogen phosphate (N-acetyl LL-E33288$\gamma_1'$:6.6 min. in the same system).

EXAMPLE 23

7-(2-Mercaptoethylamino)-4-methylcoumarin disulfide of LL-E33288$\alpha_3'$

To 0.5 mg of LL-E33288$\alpha_3'$ in 0.5 ml of acetonitrile at −15° C. was added 1.2 eq of 7-(2-mercapto-ethylamino)-4-methylcoumarin in 0.1 ml acetonitrile. One equivalent of triethylamine or one equivalent of triethylamine and one equivalent of acetic acid was added. The reaction was allowed to stir at 0° C. for one hour and the solvent was then evaporated. The residue was chromatographed on silica gel with a 5–15% methanol-in-chloroform gradient to yield the desired product. Retention time on $C_{18}$ reverse phase HPLC:5.3 min. with 60% acetonitrile/0.05M aqueous ammonium dihydrogen phosphate (LL-E33288$\alpha_3'$:4.0 min. in the same system).

EXAMPLE 24

7-(2-Mercaptoethylamino)-4-methylcoumarin disulfide of LL-E33288$\alpha_2'$

To 400 µg of LL-E33288$\alpha_2'$ in 400 µl of acetonitrile at −15° C. was added 1.2 eq of 7-(2-mercaptoethylamino)-4-methylcoumarin in 10 µl acetonitrile. One equivalent of triethylamine was added. The reaction was allowed to stir at 0° C. for one hour and the solvent was then evaporated. The residue was chromatographed on silica gel with a 5–15% methanol-in-chloroform gradient to yield the desired product. Retention time on $C_{18}$ reverse phase HPLC:5.0 min. with 64% acetonitrile/0.05M aqueous ammonium dihydrogen phosphate (LL-E33288$\alpha_2'$:7.5 min. in the same system).

EXAMPLE 25

7-(2-Mercaptoethylamino)-4-methylcoumarin disulfide of iodo LL-E33288 pseudoaglycone To 400 µg of iodo LL-E33288 pseudoaglycone in 400 µl of acetonitrile at −15° C. was added 1.2 eq of 7-(2-mercaptoethylamino)-4-methylcoumarin in 10 µl acetonitrile. One equivalent of triethylamine was added. The reaction was allowed to stir at 0° C. for one hour and the solvent was evaporated. The residue was chromatographed on silica gel with a 5–15% methanol-in-chloroform gradient to yield the desired product. Retention time on $C_{18}$ reverse phase HPLC:2.8 min. with 50% acetonitrile/0.05M aqueous ammonium dihydrogen phosphate (iodo LL-E33288 pseudoaglycone:7.9 min. in the same system).

We claim:

1. A substituted disulfide of formula Q—Sp—SS—W, prepared from a compound of formula $CH_3SSS$—W and designated as L-E33288$\alpha_1$-Br, $\alpha_1$-I, $\alpha_2$-Br, $\alpha_2$-I, $\alpha_3$-Br, $\alpha_3$-I, $\alpha_4$-Br, $\beta_1$-Br, $\beta_1$-I, $\beta_2$-Br, $\beta_2$-I, $\gamma_1$-Br, $\gamma_1$-I, $\delta_1$-I, the iodo or bromo pseudoaglycones, their dihydro or N-acyl counterparts, BBM-1675, FR-900405, FR-900406, PD114759, PD115028, CL-1577A, CL-1577B, CL-1577D, CL-1577E, CL-1724, or their N-acetyl counterparts, wherein W is

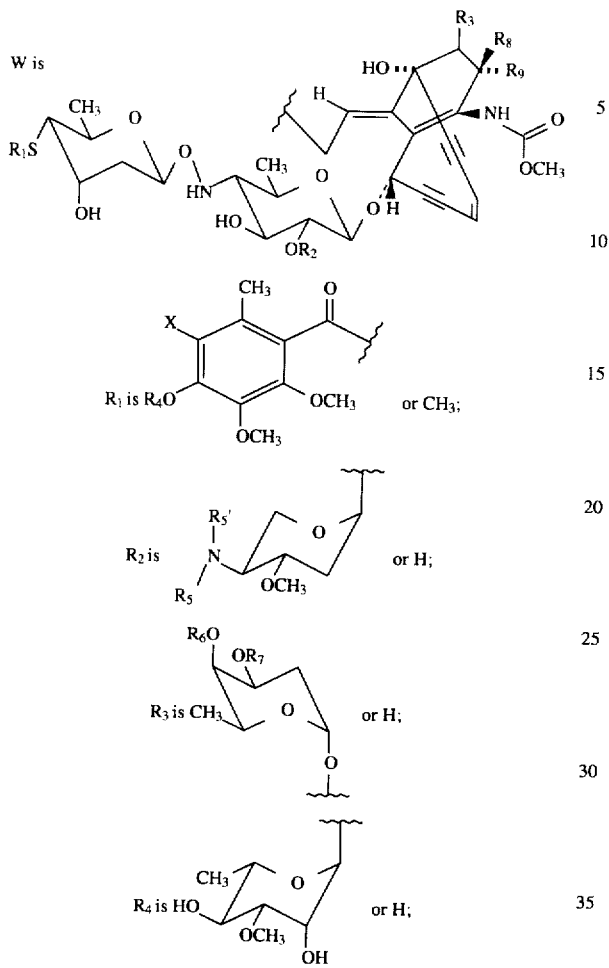

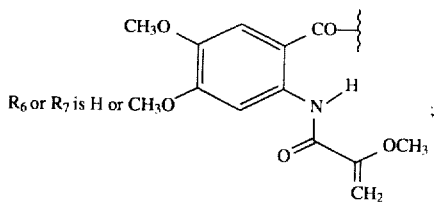

$R_5$ is $CH_3$, $C_2H_5$, or $(CH_3)_2CH$; $R_8$ is OH and $R_9$ is H, or $R_8$ and $R_9$ together is a carbonyl group; X is an iodine or bromine atom; $R_{5'}$ is a hydrogen or the group RCO, wherein R is hydrogen, $CH_3$ or a mono-substituted $C_6-C_{11}$ aryl group; Sp is a straight or branched-chain divalent or trivalent $(C_1-C_{18})$ radical, divalent or trivalent $(C_6-C_{11})$ aryl or heteroaryl radical, divalent or trivalent cyclo-alkyl $(C_3-C_{18})$ radical, divalent or trivalent $(C_6-C_{11})$aryl- or heteroaryl-alkyl $(C_4-C_{18})$ radical, divalent or trivalent $(C_3-C_{18})$ cycloalkyl-alkyl $(C_4-C_{18})$ radical, or divalent or trivalent $(C_2-C_{18})$ unsaturated alkyl radical, wherein heteroaryl is (4-methyl-coumarinyl-7-yl)amino; and wherein if Sp is a trivalent radical, it can be additionally substituted by amino, $C_1-C_{10}$ alkylamino, $C_6-C_{11}$ arylamino, heteroarylamino, carboxyl, lower alkoxy, hydroxy, thiol, or lower alkylthio groups; Q is hydrogen, halogen, amino, $C_1-C_{10}$ alkylamino, $C_1-C_{10}$ dialkylamino, piperidino, pyrrolidino, piperazino, carboxyl, carboxaldehyde, lower alkoxy, hydroxy, thiol, lower alkyldicarboxyl, —$CONHNH_2$, —$NHCONHNH_2$, —$CSNHNH_2$, —$NHCSNHNH_2$, or —$ONH_2$; with the proviso that when Sp is ethylidine, Q cannot be hydrogen.

2. A substituted disulfide of formula Q—Sp—SS—W, according to claim 1 prepared from a compound of formula $CH_3SSS$—W wherein:

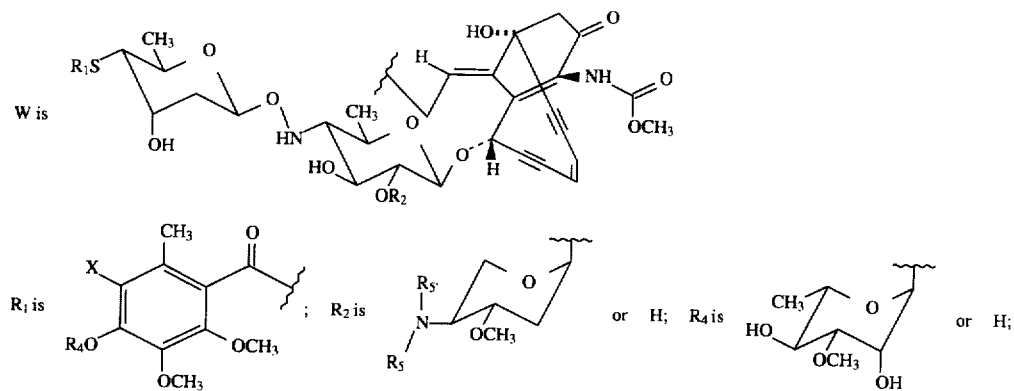

$R_5$ is $CH_3$, $C_2H_5$, or $(CH_3)_2CH$; X is an iodine or bromine atom: $R_5'$ is a hydrogen or the group RCO, wherein R is hydrogen, $CH_3$, or a mono-substituted $C_6$–$C_{11}$ aryl group wherein the substituents are as defined in claim 1; and Sp and Q are as defined in claim 1.

3. A substituted disulfide compound according to claim 2 prepared from the antitumor antibiotic of the formula $CH_3SSS$—W and designated LL-E33288$_{\gamma1}'$ having:

a) ultraviolet spectrum as shown in FIG. I;

b) a proton magnetic resonance spectrum as shown in FIG. II; and c) an infrared spectrum as shown in FIG. III.

4. A substituted disulfide compound according to claim 2 prepared from the antitumor antibiotic of the formula $CH_3SSS$—W and designated LL-E33288$_{\alpha2}'$ having:

a) a proton magnetic resonance spectrum as shown in FIG. IV; and b) a carbon-13 nuclear magnetic resonance spectrum as shown in FIG. V.

5. A substituted disulfide compound according to claim 2 prepared from the antitumor antibiotic of the formula $CH_3SSS$—W and designated LL-E33288$_{\alpha3}'$ having:

a) ultraviolet spectrum as shown in FIG. VI;

b) an infrared spectrum as shown in FIG. VII;

c) a proton magnetic resonance spectrum as shown in FIG. VIII; and d) a carbon-13 nuclear magnetic resonance spectrum as shown in FIG. IX.

6. A substituted disulfide compound according to claim 2 prepared from the antitumor antibiotic of the formula $CH_3SSS$—W and designated N-acetyl LL-E33288$_{\gamma1}'$ having:

a) ultraviolet spectrum as shown in FIG. X;

b) an infrared spectrum as shown in FIG. XI.

c) a proton magnetic resonance spectrum as shown in FIG. XII; and d) a carbon-13 nuclear magnetic resonance spectrum as shown in FIG. XIII.

7. A substituted disulfide compound according to claim 2 prepared from the antitumor antibiotic of the formula $CH_3SSS$—W and designated iodo LL-E33288 pseudoglycone having:

a) ultraviolet spectrum as shown in FIG. XIV;

b) an infrared spectrum as shown in FIG. XV;

c) a proton magnetic resonance spectrum as shown in FIG. XVI; and d) a carbon-13 nuclear magnetic resonance spectrum as shown in FIG. XVII.

8. A compound Q—Sp—SS—W according to claim 2 wherein Sp is —$CH_2$— and Q is H.

9. A compound Q—Sp—SS—W according to claim 2 wherein Sp is —$CH_2CH_2$— and Q is H.

10. A compound Q—Sp—SS—W according to claim 2 wherein Sp is —$CH_2CH(CH_3)$— and Q is H.

11. A compound Q—Sp—SS—W according to claim 2 wherein Sp is —$CH_2C(CH_3)_2$— and Q is H.

12. A compound Q—Sp—SS—W according to claim 2 wherein Sp is —$CH_2CH_2$— and Q is

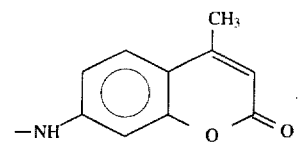

13. A compound Q—Sp—SS—W according to claim 2 wherein Sp is —$CH_2CH_2CH_2$— and Q is H.

14. A compound Q—Sp—SS—W according to claim 2 wherein Sp is —$CH_2CH_2$— and Q is —$CO_2H$.

15. A compound Q—Sp—SS—W according to claim 2 wherein Sp is —$CH_2CH_2$— and Q is

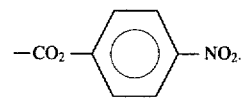

16. A compound Q—Sp—SS—W according to claim 2 wherein Sp is —$CH_2CH_2$— and Q is —$CONHNH_2$.

17. A compound Q—Sp—SS—W according to claim 2 wherein Sp is —$CH_2CH(CH_3)$— and Q is —$CO_2H$.

18. A compound Q—Sp—SS—W according to claim 2 wherein Sp is —$CH_2CH(CH_3)$— and Q is —$CONHNH_2$.

19. A compound Q—Sp—SS—W according to claim 2 wherein Sp is —$CH_2C(CH_3)_2$— and Q is —$CO_2H$.

20. A compound Q—Sp—SS—W according to claim 2 wherein Sp is —$CH_2C(CH_3)_2$— and Q is —$CONHNH_2$.

21. A compound Q—Sp—SS—W according to claim 2 wherein Sp is

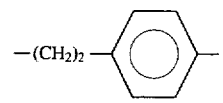

and Q is —$CO_2H$.

22. A compound Q—Sp—SS—W according to claim 2 wherein Sp is

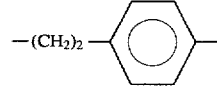

and Q is —$CONHNH_2$.

23. A compound Q—Sp—SS—W according to claim 2 wherein Sp is

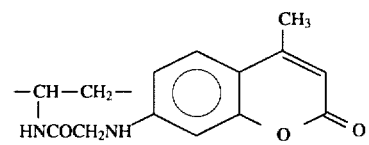

and Q is —$CONHNH_2$.

24. The ethyl disulfide of LL-E33288$_{\gamma1}$-I having the structure

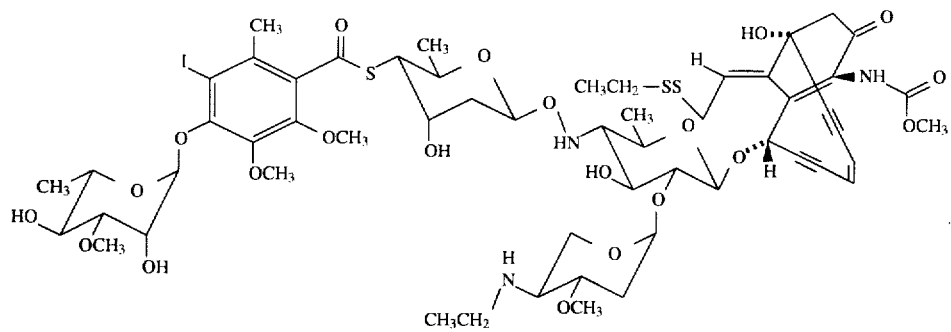
25. The propyl disulfide of LL-E33288γ₁-I having:
a) a proton magnetic resonance spectrum as shown in FIG. XXII; and
b) a mass spectrum as shown in FIG. XXIII having the structure
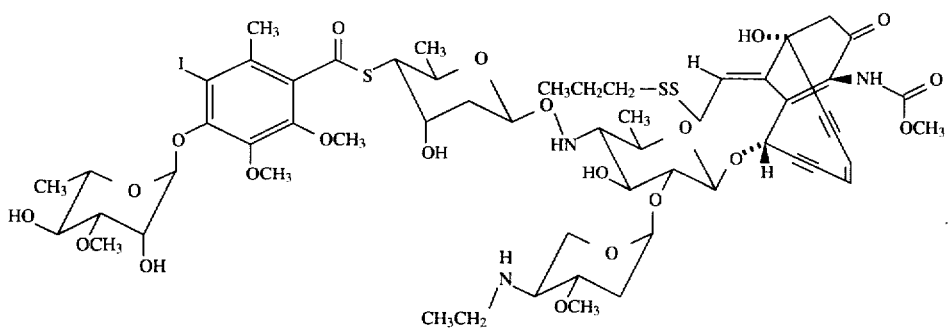
26. The 1-methyl-1-propyl disulfide of LL-E33288γ₁-I having the structure
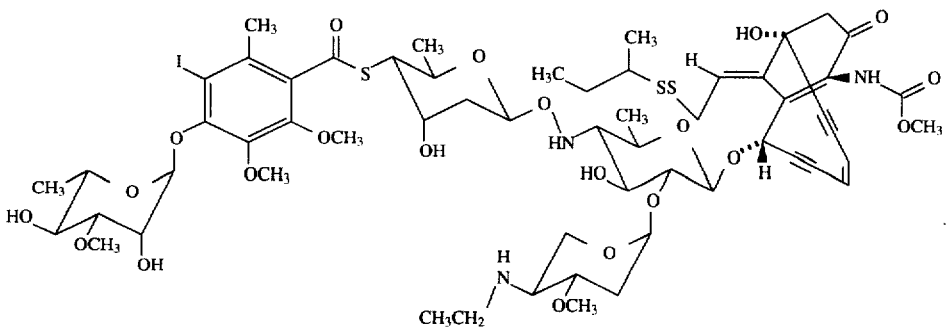
27. The t-butyl disulfide of LL-E33288γ₁-1 having the structure

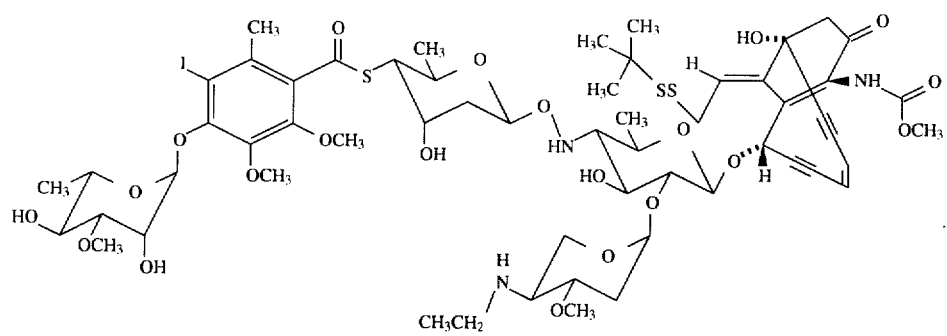
28. The 3-mercaptoproprionyl hydrazide disulfide of LL-E33288γ₁-I having the structure
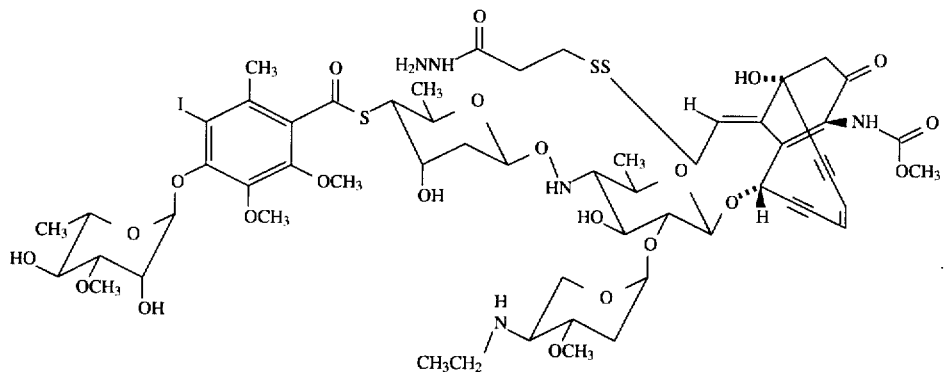
29. The 3-mercaptobutyryl hydrazide disulfide of LL-E33288α₃-I having the structure
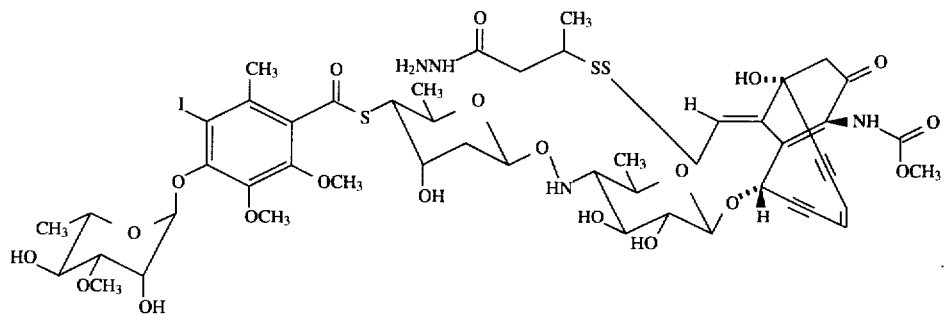
30. The 3-mercaptoisovaleryl hydrazide disulfide of N-acetyl LL-E33288γ₁-I having the structure

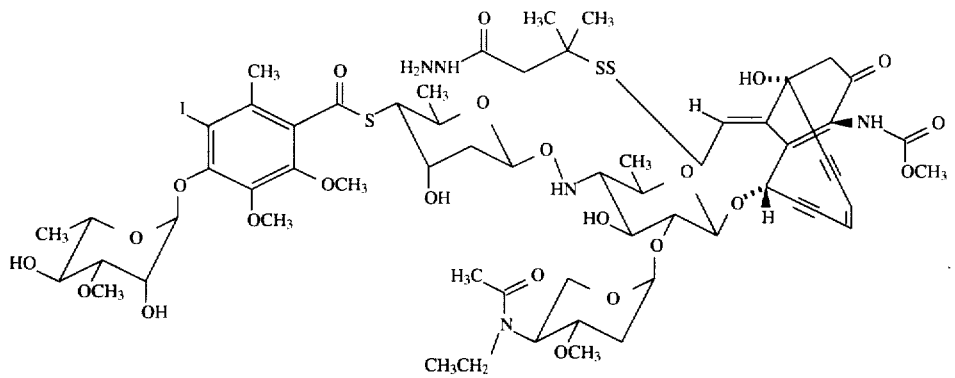

31. The p-mercaptodihydrocinnamyl hydrazide disulfide of N-acetyl LL-E33288$\gamma_1$-I having the structure

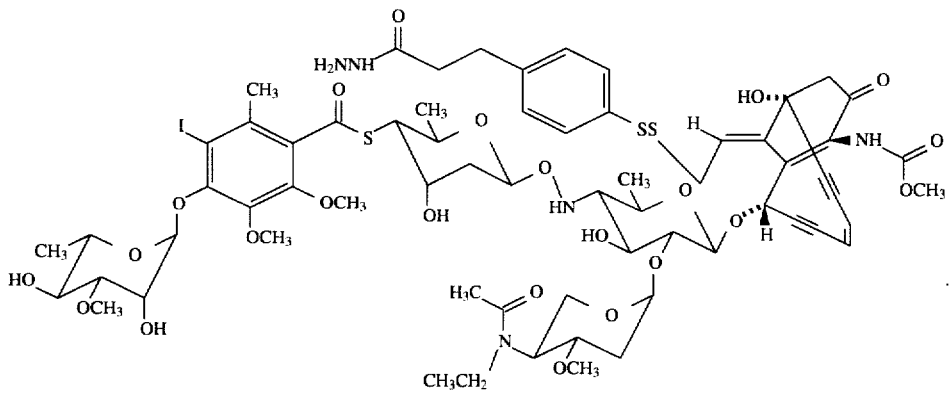

32. The compound LL-E33288$\gamma_2$-I having:

a) ultraviolet spectrum as shown in FIG. XVIII;

b) a proton magnetic resonance spectrum as shown in FIG. XIX;

c) an infrared spectrum as shown in FIG. XX;

d) a mass spectrum as shown in FIG. XXI; and e) having the structure

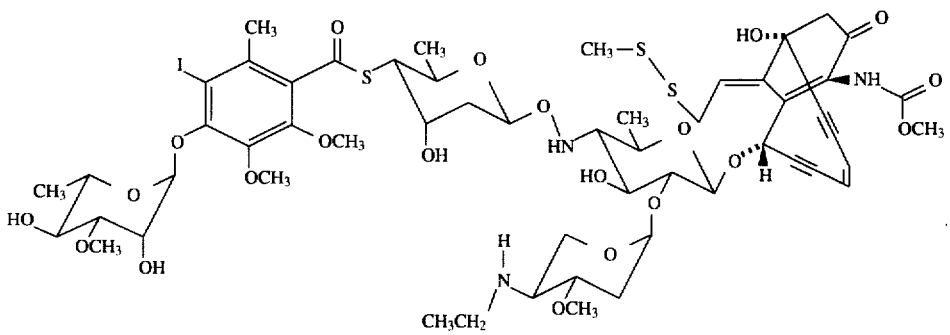

33. The compound LL-E33288$\gamma_2$-Br having the structure

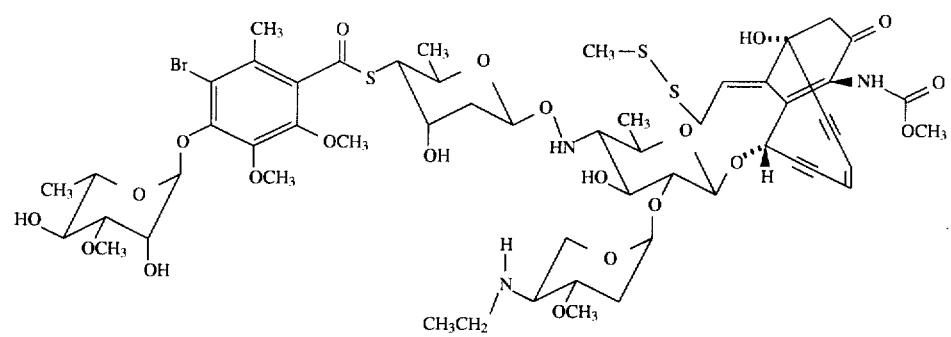

UNITED STATES PATENT AND TRADEMARK OFFICE
Certificate

Patent No. 5,606,040            Patented: February 25, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: William J. McGahren, Demarest, NJ; Martin l. Sassiver, Monsey, NY; George A. Ellestad, Pearl River, NY; Philip R. Hamann, Garnerville, NY; and Janis Upeslacis, Pomona, NY.

Signed and Sealed this Twenty-sixth Day of July 2005.

GARY GEIST
*Supervisory Patent Examiner*
Art Unit 1623